US012653120B2

(12) United States Patent
Kinkade et al.

(10) Patent No.: US 12,653,120 B2
(45) Date of Patent: Jun. 16, 2026

(54) DISEASE RESISTANT WATERMELON PLANTS

(71) Applicant: Syngenta Crop Protection AG, Basel (CH)

(72) Inventors: Matthew Kinkade, Durham, NC (US); Carine Rizzolatti, Saint-Sauveur (FR); Kishor Bhattarai, Davis, CA (US); Marc Oliver, Saint-Sauveur (FR); Ajay Sandhu, Woodland, CA (US)

(73) Assignee: SYNGENTA CROP PROTECTION AG, Basel (CH)

( * ) Notice: Subject to any disclaimer, the term of this patent is extended or adjusted under 35 U.S.C. 154(b) by 463 days.

(21) Appl. No.: 18/021,099

(22) PCT Filed: Aug. 18, 2021

(86) PCT No.: PCT/US2021/046493
§ 371 (c)(1),
(2) Date: Feb. 13, 2023

(87) PCT Pub. No.: WO2022/046487
PCT Pub. Date: Mar. 3, 2022

(65) Prior Publication Data
US 2023/0309482 A1 Oct. 5, 2023

(30) Foreign Application Priority Data
Aug. 25, 2020 (EP) .................................... 20192669

(51) Int. Cl.
| | |
|---|---|
| *A01H 1/00* | (2006.01) |
| *A01H 5/08* | (2018.01) |
| *A01H 6/34* | (2018.01) |
| *C12Q 1/6895* | (2018.01) |

(52) U.S. Cl.
CPC ............. *A01H 1/1255* (2021.01); *A01H 5/08* (2013.01); *A01H 6/342* (2018.05); *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,212,118 | B1 | 7/2012 | Brusca et al. |
| 2011/0185443 | A1 | 7/2011 | Zhang et al. |
| 2015/0101072 | A1 | 4/2015 | Lanini |
| 2016/0177404 | A1 | 6/2016 | McKernan |

FOREIGN PATENT DOCUMENTS

| | | |
|---|---|---|
| CN | 110447413 A | 11/2019 |

OTHER PUBLICATIONS

Branham et al 2017, Theoretical and Applied Genetics 130: 319-330 (Year: 2017).*
Toth et al 2007, Hungarian Agricultural Research Apr. 2007: 14-19 (Year: 2007).*
Ren et al 2015, Molecular Breeding 35: 183 (filed Feb. 13, 2023) (Year: 2015).*
Extended European Search Report for EP Application No. 21862394.0 mailed Sep. 12, 2024.
Extended ESR for EP20192669.8, mailed on Jan. 22, 2021.
Branham, S.E. et al.: "A GBS-SNP-based linkage map & quantitative trait loci (QTL) associated with resistance to *Fusarium oxysporum* f .sp. *niveum* race 2 identified in *Citrullus lanatus* var. *citroides*", Theor. Appl. Genet., (2017), vol. 130, pp. 319-330.
Ren, Yi et al.: "Genetic analysis and chromosome mapping of resistance toFusarium oxysporumf. sp.niveum(FON) race 1 and race 2 in watermelon (*Citrullus lanatus*L.)", Molecular Breeding: New Strategies in Plant Improvement, Kluwer Academic Publishers, NL, vol. 35, No. 9, Aug. 29, 2015, pp. 1-9, XP035549885, ISSN: 1380-3743, DOI: 10.1007/S11032-015-0375-5.
International Search Report for International Application No. PCT/US2021/046493 mailed Feb. 15, 2022.
Palkin M.V., "Search for Source of Watermelon Resistance to Fusarium," Plant protection and Quarantine, 2014, No. 7, pp. 23-25. (English language abstract at end of document).

* cited by examiner

*Primary Examiner* — Brent T Page
*Assistant Examiner* — Aleksandar Radosavljevic
(74) *Attorney, Agent, or Firm* — Karen A. Magri

(57) ABSTRACT

The present invention relates to novel watermelon plants displaying an increased resistance to *Fusarium oxysporum* f. sp. *niveum* race 2 infection. The present invention also relates to seeds and parts of said plants, for example fruits. The present invention further relates to methods of making and using such seeds and plants. The present invention also relates to novel genetic sequences associated with said increased resistance and to molecular markers associated with said novel genetic sequences.

19 Claims, 1 Drawing Sheet

Specification includes a Sequence Listing.

Illustrative pictures of the FON 2 phenotypes associated with the disease scoring described in Example 2C.
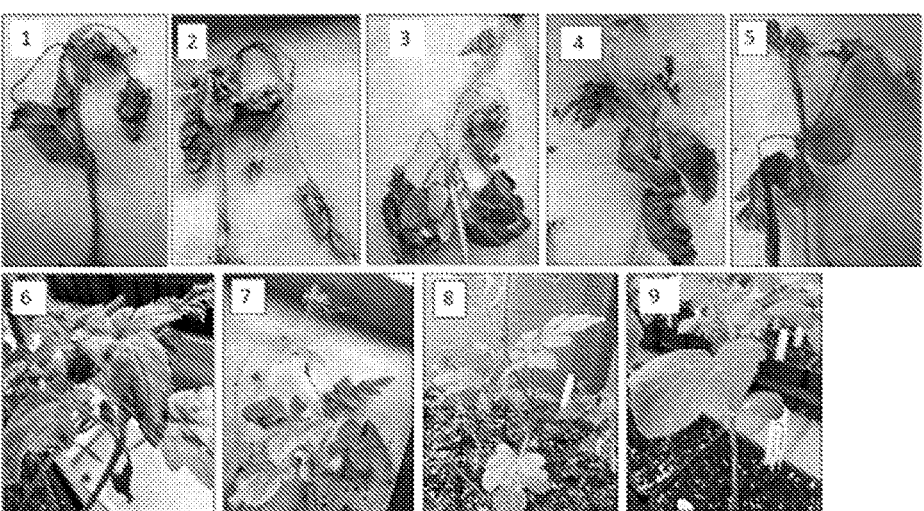

SEQUENCE LISTING

```
<160> NUMBER OF SEQ ID NOS: 75

<210> SEQ ID NO 1
<211> LENGTH: 190
<212> TYPE: DNA
<213> ORGANISM: Citrullus lanatus
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (146)..(148)
<223> OTHER INFORMATION: n is a, c, g, or t

<400> SEQUENCE: 1
ttaaataaat ttaaattagt acaacatcta gcttgtttta ctcttttgct ttttgaatta      60
catttttact aaaaaaaaaa gaaaaaanct cttaaacntt tttttttaaan aaaacttaag     120 tttttattgt ggccaatgtg tatatnnnta tattgatgga ttgaagagcc aactaagcca     180
tcaaaattga                                                            190

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
acaacatcta gcttgtttta c                                                21

<210> SEQ ID NO 3
<211> LENGTH: 14
<212> TYPE: DNA
<213> ORGANISM: Artificial Sequence
<220> FEATURE:
<223> OTHER INFORMATION: Probe

<400> SEQUENCE: 3
cacattggcc acaa                                                        14

<210> SEQ ID NO 4
<211> LENGTH: 17
<212> TYPE: DNA
<213> ORGANISM: Artificial Sequence
<220> FEATURE:
<223> OTHER INFORMATION: Probe

<400> SEQUENCE: 4
atacacattg gccataa                                                     17

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
```

-continued ggctcttcaa tccatca                                                          17

<210> SEQ ID NO 6
<211> LENGTH: 178
<212> TYPE: DNA
<213> ORGANISM: Citrullus lanatus
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t

<400> SEQUENCE: 6
tcatcatttt cttnttttct accaccatgg acatgaagaa gtttacctgc gccntccttg     60
tcgccaccgc caccgtgagt gctgctatgg cctccggtga aggcccggct cccgcaccca    120
gcccatcctc cggcgaagcc tcatctgcag ccgctttgca agctgttgga gccttcnt      178

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
accaccatgg acatgaagaa gt                                                    22

<210> SEQ ID NO 8
<211> LENGTH: 16
<212> TYPE: DNA
<213> ORGANISM: Artificial Sequence
<220> FEATURE:
<223> OTHER INFORMATION: Probe

<400> SEQUENCE: 8
aggatgggct gggtgc                                                           16

<210> SEQ ID NO 9
<211> LENGTH: 14
<212> TYPE: DNA
<213> ORGANISM: Artificial Sequence
<220> FEATURE:
<223> OTHER INFORMATION: Probe

<400> SEQUENCE: 9
atgggccggg tgcg                                                             14

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
caaagcggct gcagatgag                                                        19

<210> SEQ ID NO 11

```
<211> LENGTH: 284
<212> TYPE: DNA
<213> ORGANISM: Citrullus lanatus
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (107)..(117)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (213)..(214)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t

<400> SEQUENCE: 11
atattttcat anaaattaac tccaaactaa aaggagatat tctaagattt actaaaantn      60
nataanctaa atttgaatat ttaaaantac atagactaaa attgtannnn nnnnnnntac     120
agattattaa atgatatttt aacaaaacaa ttnaaaaaga ataccctctt cttcatttct     180
ctngcntttt tcantttctg tctcgaaaaa aannaaaaaa ataaaattgt tttgtaaatt     240
ntctttcata catcgaaccg tgtaaaacta tctagcgagt aatg                      284

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
tccaaactaa aaggagatat tc                                               22

<210> SEQ ID NO 13
<211> LENGTH: 19
```

```
<212> TYPE: DNA
<213> ORGANISM: Artificial Sequence
<220> FEATURE:
<223> OTHER INFORMATION: Probe

<400> SEQUENCE: 13
tgaagaagag ggtattctt                                                      19

<210> SEQ ID NO 14
<211> LENGTH: 19
<212> TYPE: DNA
<213> ORGANISM: Artificial Sequence
<220> FEATURE:
<223> OTHER INFORMATION: Probe

<400> SEQUENCE: 14
atgaagaaga gggctattc                                                      19

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
tacacggttc gatgtatg                                                       18

<210> SEQ ID NO 16
<211> LENGTH: 122
<212> TYPE: DNA
<213> ORGANISM: Citrullus lanatus
<220> FEATURE:
<221> NAME/KEY: misc_feature
<222> LOCATION: (10)..(10)
<223> OTHER INFORMATION: n is a, c, g, or t

<400> SEQUENCE: 16
acgccagatn gaagccagat cgttgcggtc aggtaggtgc ctggtgggaa agtgacgtag        60
cagcgagaag gcgaggggca gctgttgatg gcggactgga tggcggcggt gtcgtagtgg       120
ag                                                                       122

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
cgttgcggtc aggtaggt                                                       18

<210> SEQ ID NO 18
<211> LENGTH: 19
<212> TYPE: DNA
<213> ORGANISM: Artificial Sequence
<220> FEATURE:
<223> OTHER INFORMATION: Probe

<400> SEQUENCE: 18
ctggtgggaa agtgacgta                                                      19

<210> SEQ ID NO 19
<211> LENGTH: 17
<212> TYPE: DNA
```

<213> ORGANISM: Artificial Sequence
<220> FEATURE:
<223> OTHER INFORMATION: Probe

<400> SEQUENCE: 19
tggtgggaac gtgacgt                                                                                                      17

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
catccagtcc gccatcaaca g                                                                                                 21

<210> SEQ ID NO 21
<211> LENGTH: 153
<212> TYPE: DNA
<213> ORGANISM: Citrullus lanatus

<400> SEQUENCE: 21
gataattaat cttgccttgg acgagccaac catagggaac tcaaagctcg aagcctatga        60
aaatattcag caatggctaa taaacatctt gcagcttgtc gagttgtcaa catttgttgc       120
aatcggtgaa tcgtttggtg tctcaaattc tct                                    153

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
acgagccaac catagggaac tc                                                                                                22

<210> SEQ ID NO 23
<211> LENGTH: 18
<212> TYPE: DNA
<213> ORGANISM: Artificial Sequence
<220> FEATURE:
<223> OTHER INFORMATION: Probe

<400> SEQUENCE: 23
actcgacaag ctgcaaga                                                                                                     18

<210> SEQ ID NO 24
<211> LENGTH: 18
<212> TYPE: DNA
<213> ORGANISM: Artificial Sequence
<220> FEATURE:
<223> OTHER INFORMATION: Probe

<400> SEQUENCE: 24
ctcgacaagc agcaagat                                                                                                     18

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25

```
cgattcaccg attgcaacaa atgt                                                24

<210> SEQ ID NO 26
<211> LENGTH: 246
<212> TYPE: DNA
<213> ORGANISM: Citrullus lanatus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t

<400> SEQUENCE: 26
nttttttttc tttcttcttt ctctctttgc aaatattaat cctcaatgaa aacagagttn     60
aagtattgac atcttgttta tatgttaatt attgtttaaa catagtgaat tttcnatctc    120
ttaaaatctt ataacccaat aggtgtatca attaaaatac tatgaataaa tctagatttt    180
ttctcggtga ttcangacta ttttcactaa attctaatta aagtcaattc aaaattacct    240
aaacaa                                                               246

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
ctctctttgc aaatattaat cc                                                22

<210> SEQ ID NO 28
<211> LENGTH: 19
<212> TYPE: DNA
<213> ORGANISM: Artificial Sequence
<220> FEATURE:
<223> OTHER INFORMATION: Probe

<400> SEQUENCE: 28
tgatacacct attgggtta                                                    19

<210> SEQ ID NO 29
<211> LENGTH: 18
<212> TYPE: DNA
<213> ORGANISM: Artificial Sequence
<220> FEATURE:
<223> OTHER INFORMATION: Probe

<400> SEQUENCE: 29
ttgatacacc tattggct                                                     18

<210> SEQ ID NO 30
<211> LENGTH: 24
<212> TYPE: DNA
<213> ORGANISM: Artificial Sequence
<220> FEATURE:
```

<223> OTHER INFORMATION: Primer

<400> SEQUENCE: 30
tgactttaat tagaatttag tgaa                                                                            24

<210> SEQ ID NO 31
<211> LENGTH: 117
<212> TYPE: DNA
<213> ORGANISM: Citrullus lanatus

<400> SEQUENCE: 31
aaaatgaata gggtatctaa ccctagaatt tagatgaaat gagacagaaa atccgttgga         60
caactaaaaa attagctgaa gaactctagc aaagccatca gtggttacct ttttgga           117

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
ccctagaatt tagatgaaat gag                                                                             23

<210> SEQ ID NO 33
<211> LENGTH: 17
<212> TYPE: DNA
<213> ORGANISM: Artificial Sequence
<220> FEATURE:
<223> OTHER INFORMATION: Probe

<400> SEQUENCE: 33
ccgttggaca actaaaa                                                                                    17

<210> SEQ ID NO 34
<211> LENGTH: 16
<212> TYPE: DNA
<213> ORGANISM: Artificial Sequence
<220> FEATURE:
<223> OTHER INFORMATION: Probe

<400> SEQUENCE: 34
cgttggacaa ctcaaa                                                                                     16

<210> SEQ ID NO 35
<211> LENGTH: 17
<212> TYPE: DNA
<213> ORGANISM: Artificial Sequence
<220> FEATURE:
<223> OTHER INFORMATION: Primer

<400> SEQUENCE: 35
tggctttgct agagttc                                                                                    17

<210> SEQ ID NO 36
<211> LENGTH: 137
<212> TYPE: DNA
<213> ORGANISM: Citrullus lanatus
<220> FEATURE:
<221> NAME/KEY: misc_feature
<222> LOCATION: (7)..(7)
<223> OTHER INFORMATION: n is a, c, g, or t

<400> SEQUENCE: 36
atgaagnatt tgatgtacac tcggaagatg aatcagtaag tccaattttc ctttctccac         60

-continued agtattaata tttcatagta actttgttgt attagagctt tgtcgtcgga tgccactatt        120
ttccgttgtc acatgat                                                      137

<210> SEQ ID NO 37
<211> LENGTH: 25
<212> TYPE: DNA
<213> ORGANISM: Artificial Sequence
<220> FEATURE:
<223> OTHER INFORMATION: Primer

<400> SEQUENCE: 37
tcggaagatg aatcagtaag tccaa                                              25

<210> SEQ ID NO 38
<211> LENGTH: 20
<212> TYPE: DNA
<213> ORGANISM: Artificial Sequence
<220> FEATURE:
<223> OTHER INFORMATION: Probe

<400> SEQUENCE: 38
tcctttctcc acagtattaa                                                   20

<210> SEQ ID NO 39
<211> LENGTH: 19
<212> TYPE: DNA
<213> ORGANISM: Artificial Sequence
<220> FEATURE:
<223> OTHER INFORMATION: Probe

<400> SEQUENCE: 39
cctttctcca cggtattaa                                                    19

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
agtggcatcc gacgacaaag                                                   20

<210> SEQ ID NO 41
<211> LENGTH: 211
<212> TYPE: DNA
<213> ORGANISM: Citrullus lanatus
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t

<400> SEQUENCE: 41
agatcatcat atctcatttc cctcttcctt gcagcctcag ttagcgctgt tttaacaagt        60
ctttttgcaa ttccctgagt ttgtcaaaaa ggatggagtg atcagatcaa tgctatgagc       120
atatacagaa gaaacttaag tacttaagaa ngcaacgtac tgctcttggg ttattataca       180
caatctcgac agcttgttga ttngttagat g                                      211

<210> SEQ ID NO 42

-continued

```
<211> LENGTH: 22
<212> TYPE: DNA
<213> ORGANISM: Artificial Sequence
<220> FEATURE:
<223> OTHER INFORMATION: Primer

<400> SEQUENCE: 42
cctcttcctt gcagcctcag tt                                                22

<210> SEQ ID NO 43
<211> LENGTH: 18
<212> TYPE: DNA
<213> ORGANISM: Artificial Sequence
<220> FEATURE:
<223> OTHER INFORMATION: Probe

<400> SEQUENCE: 43
tccctgagtt tgtcaaaa                                                     18

<210> SEQ ID NO 44
<211> LENGTH: 21
<212> TYPE: DNA
<213> ORGANISM: Artificial Sequence
<220> FEATURE:
<223> OTHER INFORMATION: Probe

<400> SEQUENCE: 44
caattccctg agtttatcaa a                                                 21

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
tgtcgagatt gtgtataata accca                                             25

<210> SEQ ID NO 46
<211> LENGTH: 113
<212> TYPE: DNA
<213> ORGANISM: Citrullus lanatus
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t

<400> SEQUENCE: 46
taatataact ctcctaaatg accgtttaat tagtcactca aaaagcccaa accaacatcg       60
aaaagatcct acncnaccaa agtgacgcca aacacaagat ggtctcttta aca             113

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
accgtttaat tagtcactca a                                                 21
```

<210> SEQ ID NO 48
<211> LENGTH: 17
<212> TYPE: DNA
<213> ORGANISM: Artificial Sequence
<220> FEATURE:
<223> OTHER INFORMATION: Probe

<400> SEQUENCE: 48
ccaacatcga aaagatc                                          17

<210> SEQ ID NO 49
<211> LENGTH: 16
<212> TYPE: DNA
<213> ORGANISM: Artificial Sequence
<220> FEATURE:
<223> OTHER INFORMATION: Probe

<400> SEQUENCE: 49
ccaacatcga aacgat                                           16

<210> SEQ ID NO 50
<211> LENGTH: 16
<212> TYPE: DNA
<213> ORGANISM: Artificial Sequence
<220> FEATURE:
<223> OTHER INFORMATION: Primer

<400> SEQUENCE: 50
gtttggcgtc actttg                                           16

<210> SEQ ID NO 51
<211> LENGTH: 310
<212> TYPE: DNA
<213> ORGANISM: Citrullus lanatus
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t

<400> SEQUENCE: 51

-continued

```
atgttgatcc taatctttta agcatttgtt tacttatttt aaagcattaa acttnatact      60
cataacttaa agtgtttggt ttaactttt aaatgtttaa ttttaaaaat aaatcatttt      120
agnaaaaaaa ttaaagtgtt tgacgancan tcaaaattgt ttttaaaata cttttaaaat      180
taattttaaa tcgattntng ttaatgaaag ntggttttta gttaaancat agtgtttggg      240
tttatatttt tgttaacngt gattgaaaac aaagtttgtt tggatgcact aaatgtgatt      300
tagatagatg                                                           310

<210> SEQ ID NO 52
<211> LENGTH: 26
<212> TYPE: DNA
<213> ORGANISM: Artificial Sequence
<220> FEATURE:
<223> OTHER INFORMATION: Primer

<400> SEQUENCE: 52
agcatttgtt tacttatttt aaagca                                          26

<210> SEQ ID NO 53
<211> LENGTH: 21
<212> TYPE: DNA
<213> ORGANISM: Artificial Sequence
<220> FEATURE:
<223> OTHER INFORMATION: Probe

<400> SEQUENCE: 53
ttggtttaac tttttaaatg t                                               21

<210> SEQ ID NO 54
<211> LENGTH: 20
<212> TYPE: DNA
<213> ORGANISM: Artificial Sequence
<220> FEATURE:
<223> OTHER INFORMATION: Probe

<400> SEQUENCE: 54
tggtttaact ttttaagtgt                                                 20

<210> SEQ ID NO 55
<211> LENGTH: 17
<212> TYPE: DNA
<213> ORGANISM: Artificial Sequence
<220> FEATURE:
<223> OTHER INFORMATION: Primer

<400> SEQUENCE: 55
agtgcatcca aacaaac                                                    17

<210> SEQ ID NO 56
<211> LENGTH: 171
<212> TYPE: DNA
<213> ORGANISM: Citrullus lanatus
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t

<400> SEQUENCE: 56
```
tgaagaacna tactcaatct acaccggtta ctgaagttaa gaactcgaat caaactgaat        60
cgaagaatgc ccctccggtg gtagatgatc aggttaagag ttcggggctg aaaccgattc       120
catngaataa tggaagttct agggcagagg agaaaaangt atcgacgaat t               171

<210> SEQ ID NO 57
<211> LENGTH: 24
<212> TYPE: DNA
<213> ORGANISM: Artificial Sequence
<220> FEATURE:
<223> OTHER INFORMATION: Primer

<400> SEQUENCE: 57
acaccggtta ctgaagttaa gaac                                               24

<210> SEQ ID NO 58
<211> LENGTH: 18
<212> TYPE: DNA
<213> ORGANISM: Artificial Sequence
<220> FEATURE:
<223> OTHER INFORMATION: Probe

<400> SEQUENCE: 58
ctccggtggt agatgatc                                                      18

<210> SEQ ID NO 59
<211> LENGTH: 17
<212> TYPE: DNA
<213> ORGANISM: Artificial Sequence
<220> FEATURE:
<223> OTHER INFORMATION: Probe

<400> SEQUENCE: 59
ctccggtggt ggatgat                                                       17

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
tcctctgccc tagaacttcc att                                                23

<210> SEQ ID NO 61
<211> LENGTH: 208
<212> TYPE: DNA
<213> ORGANISM: Citrullus lanatus
<220> FEATURE:
<221> NAME/KEY: misc_feature
<222> LOCATION: (117)..(117)
<223> OTHER INFORMATION: n is a, c, g, or t

<400> SEQUENCE: 61
caaaaaaatc ccagaatgct ctccgactct ggtctacatt tctgactaaa agtttcacct        60
gtttctctaa tcaaaaactg tatttcatga cttgatcttt gtattgcaat aatcttnaag       120
tctaaggaat atcgaatgga taaaatgggc ccttctgtaa ttgcatcagt ggtataagca       180
acagcaggat taaacggaac agttttcc                                          208

<210> SEQ ID NO 62
<211> LENGTH: 24
<212> TYPE: DNA

-continued

```
<213> ORGANISM: Artificial Sequence
<220> FEATURE:
<223> OTHER INFORMATION: Primer

<400> SEQUENCE: 62
ctccgactct ggtctacatt tctg                                          24

<210> SEQ ID NO 63
<211> LENGTH: 18
<212> TYPE: DNA
<213> ORGANISM: Artificial Sequence
<220> FEATURE:
<223> OTHER INFORMATION: Probe

<400> SEQUENCE: 63
cccattttat ccattcga                                                 18

<210> SEQ ID NO 64
<211> LENGTH: 21
<212> TYPE: DNA
<213> ORGANISM: Artificial Sequence
<220> FEATURE:
<223> OTHER INFORMATION: Probe

<400> SEQUENCE: 64
agggcccatt ttatctattc g                                             21

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65
cctgctgttg cttataccac tga                                           23

<210> SEQ ID NO 66
<211> LENGTH: 149
<212> TYPE: DNA
<213> ORGANISM: Citrullus lanatus
<220> FEATURE:
<221> NAME/KEY: misc_feature
<222> LOCATION: (84)..(85)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t

<400> SEQUENCE: 66
tctttctctc tcatagtctg tcctctgtac cttgcacaac tccccctcac accttctttt     60
tcataaatgg ggaaaatgaa aaannggaaa tngagattng aaattgttga aaagggaaaa    120
tgaaccatga tattggcatt tacggagga                                     149

<210> SEQ ID NO 67
<211> LENGTH: 22
<212> TYPE: DNA
<213> ORGANISM: Artificial Sequence
<220> FEATURE:
<223> OTHER INFORMATION: Primer

<400> SEQUENCE: 67
```
tcctctgtac cttgcacaac tc                                                           22

<210> SEQ ID NO 68
<211> LENGTH: 19
<212> TYPE: DNA
<213> ORGANISM: Artificial Sequence
<220> FEATURE:
<223> OTHER INFORMATION: Probe

<400> SEQUENCE: 68
tcattttccc catttatga                                                               19

<210> SEQ ID NO 69
<211> LENGTH: 21
<212> TYPE: DNA
<213> ORGANISM: Artificial Sequence
<220> FEATURE:
<223> OTHER INFORMATION: Probe

<400> SEQUENCE: 69
tttcattttc cctatttatg a                                                            21

<210> SEQ ID NO 70
<211> LENGTH: 25
<212> TYPE: DNA
<213> ORGANISM: Artificial Sequence
<220> FEATURE:
<223> OTHER INFORMATION: Primer

<400> SEQUENCE: 70
catggttcat ttccctttt caaca                                                         25

<210> SEQ ID NO 71
<211> LENGTH: 113
<212> TYPE: DNA
<213> ORGANISM: Citrullus lanatus

<400> SEQUENCE: 71
tagtcatatc ctgaaacctt tcgaactccg aggataaaca agaagcatgg attagaagtg                  60
gaaacaacaa tcacattatg tccaactgct cccaagctta taccgatatt atc                        113

<210> SEQ ID NO 72
<211> LENGTH: 23
<212> TYPE: DNA
<213> ORGANISM: Artificial Sequence
<220> FEATURE:
<223> OTHER INFORMATION: Primer

<400> SEQUENCE: 72
tcgaactccg aggataaaca aga                                                          23

<210> SEQ ID NO 73
<211> LENGTH: 16
<212> TYPE: DNA
<213> ORGANISM: Artificial Sequence
<220> FEATURE:
<223> OTHER INFORMATION: Probe

<400> SEQUENCE: 73
cacttctaat ccatgc                                                                  16

<210> SEQ ID NO 74
<211> LENGTH: 16
<212> TYPE: DNA

-continued

```
<213> ORGANISM: Artificial Sequence
<220> FEATURE:
<223> OTHER INFORMATION: Probe

<400> SEQUENCE: 74
cacttctaac ccatgc                                                    16

<210> SEQ ID NO 75
<211> LENGTH: 24
<212> TYPE: DNA
<213> ORGANISM: Artificial Sequence
<220> FEATURE:
<223> OTHER INFORMATION: Primer

<400> SEQUENCE: 75
gggagcagtt ggacataatg tgat                                           24
```

DISEASE RESISTANT WATERMELON PLANTS

RELATED APPLICATION INFORMATION

This application is a national stage entry under 35 U.S.C. § 371 of International Application No. PCT/US2021/046493, filed 18 Aug. 2021, which claims the benefit of EP Application Serial No. 20192669.8, filed 25 Aug. 2020, the contents of which are incorporated herein by reference in their entirety.

STATEMENT REGARDING ELECTRONIC SUBMISSION OF A SEQUENCE LISTING

A Sequence Listing in ASCII text format, submitted under 37 C.F.R. § 1.821, entitled "82148-WO_23Aug.2021_Sequence-listing.txt" 19.2 KB (19,711 bytes) in size, generated on Dec. 22, 2022 and filed via EFS-Web is provided in lieu of a paper copy. This Sequence Listing is hereby incorporated by reference into the specification for its disclosures.

FIELD OF THE INVENTION

The present invention relates to novel watermelon plants displaying an increased resistance to *Fusarium oxysporum* f. sp. *niveum* race 2 infection. The present invention also relates to seeds and parts of said plants, for example fruits. The present invention further relates to methods of making and using such seeds and plants. The present invention also relates to novel genetic sequences associated with said increased resistance and to molecular markers associated with said novel genetic sequences.

BACKGROUND OF THE INVENTION

Watermelon [*Citrullus lanatus* (Thunb.) Matsum and Nakai] is an important specialty crop is believed to have originated from Southern Africa in an area near the Kalahari Desert (Dane & Liu, 2007). It is a common crop in all major agriculture production areas and represented a world production of 103,931,337 tonnes in 2018 (derived from data supplied by the Food and Agriculture Organization). The United States production alone was worth up to 561 million of US dollars in 2019 (USDA Vegetables 2019 Summary).

Plant pathogens are known to cause massive damage to important crops, including watermelon, resulting in significant agricultural losses with widespread consequences for both the food supply and other industries that rely on plant materials. As such, there is a long felt need to reduce the incidence and/or impact of agricultural pests on crop production. An example of such pathogens is the *Fusarium oxysporum* (*F. oxysporum*) genus of plant fungi. *F. oxysporum* is known to devastate various crop plants including, but not limited to pea, banana, cotton, tomato, watermelon and others. *F. oxysporum* is characterized by several different specialized forms, which are referred to as formae specialis (f. sp.), each of which infect a variety of hosts to cause disease. There are at least 48 different formae specialis of *F. oxysporum*.

One particular formae specialis of *F. oxysporum* is *F. oxysporum* f. sp. *niveum* (FON), which infects various watermelon types of the species *Citrullus lanatus* subsp. *lanatus*, which includes Asian protected, Charleston Grey, Crimson Sweet, Sugar Baby, Jubilee, and Allsweet types.

Several races have been identified for FON, and include races 0, 1, 2, and 3 (Martyn and Bruton, 1989; Zhou et al., 2010).

Some sources of resistance have been described against the FON 2 race.

U.S. Pat. Nos. 7,550,652, 8,173,873 and 8,212,118 discloses watermelon lines SP-4, SP-5 and SP-6 respectively, all described as being tolerant or intermediate resistant to FON 2 infestations.

U.S. patent application Ser. No. 14/507,277 discloses watermelon plants having FON 2 resistance while retaining desirable commercial characteristics. The FON 2 trait is derived from accession PI-296341-FR, a long-known potential source of FON 2 resistance in watermelon (Martyn and Netzer, 1991).

Wechter et al. (2012) describe a number of additional potential sources for FON 2 resistance in watermelon breeding.

Ren et al. (2015) report one FON 2 resistance QTL on chromosome 9 derived from *C. lanatus* subsp. *citroides* accession PI296341-FR and one FON 2 resistance QTL on chromosome 10 derived from the susceptible elite line 97103.

Branham et al. (2017) also report QTLs associated with FON 2 resistance derived from *C. lanatus* subsp. *citroides* accession USVL246-FR2, a major one being located on chromosome 9 while a minor one was located on chromosome 10.

Despite the existence of potential sources for a FON 2 resistance trait in watermelon, there are currently no FON 2 tolerant or resistant commercial material with acceptable horticultural quality (producing sweet, edible fruits) available to watermelon growers (Meru and McGregor, 2016; Pal et al., 2020). Therefore, there remains a need for novel sources of resistance against FON 2 strains, which would provide for easier and better FON 2 resistance management while being adaptable into commercially relevant watermelon germplasm.

SUMMARY OF THE INVENTION

The present invention addresses the need for an improved resistance to FON 2 strains by including and providing novel watermelon plants comprising an increased FON 2 resistance trait. By identifying one QTL associated with increased FON 2 resistance in a breeding population and by introgressing its corresponding sequence into elite watermelon plants, the FON 2 resistance capability of the watermelon plant was greatly increased, which has a positive impact on overall plant performance. The FON 2 resistance QTL and its corresponding introgressed sequence, located on chromosome 10 (QTL10), is of semi-dominant nature, hence one copy of the sequence already provides an improved FON 2 resistance phenotype.

Altogether, the characteristics of the improved FON 2 resistant watermelon plant disclosed within the present invention provide a watermelon grower with novel solutions to enhance economic and commercial efficiency when deploying watermelon varieties in a FON 2 pressured field.

In a first embodiment, the invention provides a cultivated watermelon plant, preferably a cultivated *Citrullus lanatus* subsp. *lanatus* plant resistant to *Fusarium oxysporum* f. sp. *niveum* race 2 (FON 2) infection, comprising in its genome an introgressed sequence from *C. lanatus* subsp. *citroides* which confers resistance to FON 2, wherein said introgressed sequence is located on chromosome 10 and comprises at least one of the following SNP markers:

a) a G genotype in the heterozygous or homozygous state for SNP marker 1 at a position corresponding to position 129 in SEQ ID NO: 1;

b) an A genotype in the heterozygous or homozygous state for SNP marker 2 at a position corresponding to position 120 in SEQ ID NO: 6;

c) an indel genotype in the heterozygous or homozygous state for SNP marker 3 at a position corresponding to position 164 in SEQ ID NO: 11;

d) an A genotype in the heterozygous or homozygous state for SNP marker 4 at a position corresponding to position 51 in SEQ ID NO: 16;

e) an A genotype in the heterozygous or homozygous state for SNP marker 5 at a position corresponding to position 93 in SEQ ID NO: 21;

f) a C genotype in the heterozygous or homozygous state for SNP marker 6 at a position corresponding to position 135 in SEQ ID NO: 26;

g) an A genotype in the heterozygous or homozygous state for SNP marker 7 at a position corresponding to position 66 in SEQ ID NO: 31;

h) an A genotype in the heterozygous or homozygous state for SNP marker 8 at a position corresponding to position 61 in SEQ ID NO: 36;

i) a G genotype in the heterozygous or homozygous state for SNP marker 9 at a position corresponding to position 83 in SEQ ID NO: 41;

j) an A genotype in the heterozygous or homozygous state for SNP marker 10 at a position corresponding to position 64 in SEQ ID NO: 46;

k) an A genotype in the heterozygous or homozygous state for SNP marker 11 at a position corresponding to position 93 in SEQ ID NO: 51;

l) an A genotype in the heterozygous or homozygous state for SNP marker 12 at a position corresponding to position 83 in SEQ ID NO: 56;

m) a G genotype in the heterozygous or homozygous state for SNP marker 13 at a position corresponding to position 138 in SEQ ID NO: 61;

n) a G genotype in the heterozygous or homozygous state for SNP marker 14 at a position corresponding to position 69 in SEQ ID NO: 66; and/or o) an A genotype in the heterozygous or homozygous state for SNP marker 15 at a position corresponding to position 51 in SEQ ID NO: 71.

In a further embodiment of the invention, said FON 2 resistance-conferring introgressed sequence comprises at least one of SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, and/or SEQ ID NO: 71 or a sequence that is at least 80%, preferably at least 85%, more preferably at least 90%, even more preferably at least 95% identical to one or more of said sequences.

In a further embodiment of the invention, said plant is heterozygous for said at least one SNP marker. In a further embodiment of the invention, said plant is homozygous for said at least one SNP marker.

In a further embodiment of the invention, said introgressed sequence is comprised in *Citrullus lanatus* subsp. *citroides* accession RCAT055816 or in watermelon plant 18WMH505078, representative seed of which is deposited under NCIMB Accession No. 43627, or a progeny or an ancestor thereof.

In a further embodiment, the invention provides a plant according to any of the preceding embodiments wherein said plant is obtained by crossing *Citrullus lanatus* subsp. *citroides* accession RCAT055816 or watermelon plant 18WMH505078, representative seed of which is deposited under NCIMB Accession No. 43627, or a progeny or an ancestor thereof, with a watermelon plant that does not contain said FON 2 resistance-conferring introgressed sequence.

In a further embodiment, the invention provides a plant according to any of the preceding embodiments, wherein said plant is an inbred, a dihaploid, a diploid, a triploid, a tetraploid or a hybrid plant.

It is a further embodiment to provide a plant part, organ or tissue obtainable from a watermelon plant according to any of preceding embodiments, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the FON 2 resistance trait according to the invention, particularly when grown into a plant that produces fruits.

In a further embodiment, the invention provides a seed that produces a plant according to any of the preceding embodiments.

In a further embodiment, the invention provides a method for producing a cultivated watermelon plant, preferably a cultivated *Citrullus lanatus* subsp. *lanatus* plant, exhibiting resistance to FON 2 comprising the steps of a) crossing a plant according to any one of the preceding embodiments with a cultivated watermelon plant lacking said FON 2 resistance-conferring introgressed sequence;

b) selecting a progeny plant comprising said introgressed sequence located on chromosome 10 conferring resistance to FON 2, said selecting step comprising detecting at least one of the following SNP markers:

i) a G genotype in the heterozygous or homozygous state for SNP marker 1 at a position corresponding to position 129 in SEQ ID NO: 1;

ii) an A genotype in the heterozygous or homozygous state for SNP marker 2 at a position corresponding to position 120 in SEQ ID NO: 6;

iii) an indel genotype in the heterozygous or homozygous state for SNP marker 3 at a position corresponding to position 164 in SEQ ID NO: 11;

iv) an A genotype in the heterozygous or homozygous state for SNP marker 4 at a position corresponding to position 51 in SEQ ID NO: 16;

v) an A genotype in the heterozygous or homozygous state for SNP marker 5 at a position corresponding to position 93 in SEQ ID NO: 21;

vi) a C genotype in the heterozygous or homozygous state for SNP marker 6 at a position corresponding to position 135 in SEQ ID NO: 26;

vii) an A genotype in the heterozygous or homozygous state for SNP marker 7 at a position corresponding to position 66 in SEQ ID NO: 31;

viii) an A genotype in the heterozygous or homozygous state for SNP marker 8 at a position corresponding to position 61 in SEQ ID NO: 36;

ix) a G genotype in the heterozygous or homozygous state for SNP marker 9 at a position corresponding to position 83 in SEQ ID NO: 41;

x) an A genotype in the heterozygous or homozygous state for SNP marker 10 at a position corresponding to position 64 in SEQ ID NO: 46;

xi) an A genotype in the heterozygous or homozygous state for SNP marker 11 at a position corresponding to position 93 in SEQ ID NO: 51;

xii) an A genotype in the heterozygous or homozygous state for SNP marker 12 at a position corresponding to position 83 in SEQ ID NO: 56;

xiii) a G genotype in the heterozygous or homozygous state for SNP marker 13 at a position corresponding to position 138 in SEQ ID NO: 61;

xiv) a G genotype in the heterozygous or homozygous state for SNP marker 14 at a position corresponding to position 69 in SEQ ID NO: 66; and/or xv) an A genotype in the heterozygous or homozygous state for SNP marker 15 at a position corresponding to position 51 in SEQ ID NO: 71;

thereby producing a plant with enhanced resistance to FON 2.

In a further embodiment, the invention relates to the method of any of the preceding embodiments, wherein the method further comprises:

c) selfing the selected progeny or crossing the selected progeny with another watermelon plant to produce further progeny.

In a further embodiment, the invention relates to the method of the preceding embodiment, wherein further progeny are selected and selfed/crossed for 2 to 10 more generations.

In a further embodiment, the invention relates to the method of any of the preceding embodiments, wherein the plant of step a) is *Citrullus lanatus* subsp. *citroides* accession RCAT055816 or watermelon plant 18WMH505078, representative seed of which is deposited under NCIMB Accession No. 43627, or a progeny or an ancestor thereof.

In a further embodiment, the invention relates to a method for producing a F1 watermelon plant exhibiting resistance to FON 2, the method comprising crossing an inbred watermelon plant, which is a plant according to any one of the preceding embodiments, with a different inbred watermelon plant to produce F1 hybrid progeny.

In a further embodiment, the invention provides a method for identifying a cultivated watermelon plant, preferably a cultivated *Citrullus lanatus* subsp. *lanatus* plant, exhibiting resistance to FON 2 and having at least one copy of said FON 2 resistance-conferring introgressed sequence, said method comprising the step of detecting at least one of the following SNP markers:

a) a G genotype in the heterozygous or homozygous state for SNP marker 1 at a position corresponding to position 129 in SEQ ID NO: 1;

b) an A genotype in the heterozygous or homozygous state for SNP marker 2 at a position corresponding to position 120 in SEQ ID NO: 6;

c) an indel genotype in the heterozygous or homozygous state for SNP marker 3 at a position corresponding to position 164 in SEQ ID NO: 11;

d) an A genotype in the heterozygous or homozygous state for SNP marker 4 at a position corresponding to position 51 in SEQ ID NO: 16;

e) an A genotype in the heterozygous or homozygous state for SNP marker 5 at a position corresponding to position 93 in SEQ ID NO: 21;

f) a C genotype in the heterozygous or homozygous state for SNP marker 6 at a position corresponding to position 135 in SEQ ID NO: 26;

g) an A genotype in the heterozygous or homozygous state for SNP marker 7 at a position corresponding to position 66 in SEQ ID NO: 31;

h) an A genotype in the heterozygous or homozygous state for SNP marker 8 at a position corresponding to position 61 in SEQ ID NO: 36;

i) a G genotype in the heterozygous or homozygous state for SNP marker 9 at a position corresponding to position 83 in SEQ ID NO: 41;

j) an A genotype in the heterozygous or homozygous state for SNP marker 10 at a position corresponding to position 64 in SEQ ID NO: 46;

k) an A genotype in the heterozygous or homozygous state for SNP marker 11 at a position corresponding to position 93 in SEQ ID NO: 51;

l) an A genotype in the heterozygous or homozygous state for SNP marker 12 at a position corresponding to position 83 in SEQ ID NO: 56;

m) a G genotype in the heterozygous or homozygous state for SNP marker 13 at a position corresponding to position 138 in SEQ ID NO: 61;

n) a G genotype in the heterozygous or homozygous state for SNP marker 14 at a position corresponding to position 69 in SEQ ID NO: 66; and/or o) an A genotype in the heterozygous or homozygous state for SNP marker 15 at a position corresponding to position 51 in SEQ ID NO: 71;

thereby identifying a watermelon plant exhibiting resistance to FON 2.

In a further embodiment, the invention relates to the method of the preceding embodiment, wherein said method further comprises selecting a watermelon plant comprising said one or more SNP markers, and crossing the selected watermelon plant with a second watermelon plant to produce progeny watermelon plants that comprise at least one of said SNP markers and exhibits increased resistance to FON 2.

BRIEF DESCRIPTION OF THE DRAWINGS

FIG. 1 shows FON 2 pathology assay pictures representative of the disease scale used.

DETAILED DESCRIPTION OF THE INVENTION

Definitions

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

A "cultivated watermelon" or an "elite watermelon" plant is understood within the scope of the invention to refer to a plant that is no longer in the natural state but has been developed and domesticated by human care and for agricultural use and/or human consumption, and excludes wild watermelon accessions, such as *C. lanatus* subsp. *citroides* accessions. As a matter of example, in embodiments, a cultivated or elite watermelon plant according to the present invention is capable of growing fruits having red flesh and/or a Brix level better than 8, preferably better than 10. Alternatively, or additionally, the cultivated watermelon plant is a hybrid, a triploid or a tetraploid plant. Alternatively, or additionally, the cultivated watermelon plant is a triploid seedless plant. Alternatively, or additionally, the cultivated watermelon plant is a *C. lanatus* subsp. *lanatus* plant. In the context of an interspecific cross between a *C. lanatus* subsp. *lanatus* plant and a wild watermelon accession, a cultivated watermelon plant is defined as a progeny plant of said interspecific cross, wherein said progeny plant has been backcrossed at least two times against a *C. lanatus* subsp. *lanatus* plant.

An "allele" is understood within the scope of the invention to refer to alternative or variant forms of various genetic units identical or associated with different forms of a gene or of any kind of identifiable genetic determinant such as a QTL, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, chemical or structural modification, transcription regulation or post-translational modification/regulation. In a diploid cell or organism, the two alleles of a given gene or genetic element typically occupy corresponding loci on a pair of homologous chromosomes.

Relatively speaking, the term "improved FON 2 resistance" or "increased FON 2 resistance" is herein understood to mean that a plant according to the present invention, e.g. comprising an introgressed sequence from *C. lanatus* subsp. *citroides* plant which confers resistance to FON 2, wherein said introgressed sequence is located on chromosome 10 and comprises at least one of SNP markers 1 to 15, is more tolerant or more resistant to FON 2 strains when compared with a plant lacking said introgressed sequence.

"Improved FON 2 resistance" is understood within the scope of the invention to mean a watermelon plant which has a statistically significant improved resistance to FON 2 strains compared to a control watermelon plant lacking the introgressed sequence of the invention (for example as described in the Example section), using standard error and/or at P<0.05 or P<0.01 using Student's test.

"Phenotype" is understood within the scope of the invention to refer to a distinguishable characteristic(s) of a genetically controlled trait.

A "control watermelon plant" is understood within the scope of the invention to mean a watermelon plant that has the same genetic background as the cultivated watermelon plant of the present invention wherein the control plant does not have the introgressed sequence of the present invention linked to improved FON 2 resistance. In particular a control watermelon plant is a watermelon plant belonging to the same plant variety and does not comprise the introgressed sequence of the present invention. The control watermelon plant is grown for the same length of time and under the same conditions as the cultivated watermelon plant of the present invention. Plant variety is herein understood according to definition of UPOV. Thus, a control watermelon plant may be a near-isogenic line, an inbred line or a hybrid provided that they have the same genetic background as the watermelon plant of the present invention except the control plant does not have the introgressed sequence of the present invention linked to improved FON 2 resistance.

The term "trait" refers to a characteristic or a phenotype. In the context of the present invention, a FON 2 resistance trait is an improved FON 2 resistance trait. A trait may be inherited in a dominant or recessive manner, or in a partial, semi- or incomplete-dominant manner. In the context of the present invention, the FON 2 resistance-conferring introgressed sequence located on chromosome 10 is semi-dominant. A watermelon plant of the invention can therefore be heterozygous or homozygous for the trait. Furthermore, a trait may be monogenic or polygenic, or may result from the interaction of one or more genes with the environment. In the context of the present invention, the FON 2 resistance-conferring introgressed sequence located on chromosome 10 is sufficient to confer, alone, the improved FON 2 resistance trait.

The terms "hybrid", "hybrid plant", and "hybrid progeny" refer to an individual produced from genetically different parents (e.g. a genetically heterozygous or mostly heterozygous individual).

The term "inbred line" refers to a genetically homozygous or nearly homozygous population. An inbred line, for example, can be derived through several cycles of brother/sister breeding or of selfing or in dihaploid production.

The term "dihaploid line" refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially no longer segregating (stable).

The terms "triploid watermelon plant" and "tetraploid watermelon plant" refer to watermelon plants with particular ploidy levels. Triploid (also referred to as "seedless") watermelon is a true F1 hybrid between a tetraploid watermelon, as the female parent, and a diploid watermelon, as the male parent (Kihara, 1951). Diploid watermelon plants possess 22 chromosomes (2N=2X=22) whereas tetraploid watermelon plants possess 44 chromosomes (2N=4X=44). Tetraploid watermelon plants are obtained via chemical treatment of diploid watermelon plants. Chemicals such as colchicine or oryzalin are often used to induce a chromosomal duplication. When female flowers of the tetraploid watermelon plant are pollinated by the male flowers of the diploid watermelon plant, the seeds produced in the fruit of the tetraploid plant are triploid hybrid seeds. The triploid hybrid plants grown from the triploid seeds are self-infertile due to the inability of the triploid zygote to produce normal viable gametes (Fehr, 1987). Consequently, to ensure seedless watermelon fruit production, fruit set on triploid plants must be induced via chemical means, or triggered by pollination by diploid watermelon plants, sometimes referred to as diploid pollenizer plants.

The term "genetically fixed" refers to a genetic sequence which has been stably incorporated into the genome of a plant that normally does not contain said genetic sequence. When genetically fixed, the genetic sequence can be transmitted in an easy and predictable manner to other plants by sexual crosses.

The term "rootstock" refers to a plant used as a receptacle for a scion plant. Typically, the rootstock plant and the scion plant are of different genotypes. In embodiments, plants according to the present invention are used as rootstock plants.

The term "plant" or "plant part' refers hereinafter to a plant part, organ or tissue obtainable from a watermelon plant according to the invention, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the improved FON 2 resistance trait according to the invention, particularly when grown into a plant that produces fruits.

A "plant" is any plant at any stage of development.

A watermelon plant seed is a seed which grows into a watermelon plant according to any of the embodiments.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "breeding", and grammatical variants thereof, refer to any process that generates a progeny individual. Breeding can be sexual or asexual, or any combination thereof. Exemplary non-limiting types of breeding include crossings, selfing, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes. In the context of the invention, a watermelon plant comprising two identical copies of a particular introgressed sequence at a particular locus, e.g. the introgressed sequence located on chromosome 10, is homozygous on a corresponding locus.

"Heterozygous" is understood within the scope of the invention to refer to unlike alleles at one or more corresponding loci on homologous chromosomes. In the context of the invention, a watermelon plant comprising one copy of a particular introgressed sequence at a particular locus, e.g. the introgressed sequence located on chromosome 10, is heterozygous on a corresponding locus.

A "dominant" allele is understood within the scope of the invention to refer to an allele which determines the phenotype when present in the heterozygous or homozygous state. A "semi-dominant" allele is understood within the scope of the invention to refer to an allele which determines the phenotype when present in the heterozygous or homozygous state. The intensity of the phenotype is however generally higher when the allele is present in the homozygous state.

A "recessive" allele refers to an allele which determines the phenotype when present in the homozygous state only.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene, a QTL or its corresponding genetic sequence contributing to a trait.

As used herein, "marker locus" refers to a region on a chromosome, which comprises a nucleotide or a polynucleotide sequence that is present in an individual's genome and that is associated with one or more loci of interest, which may comprise a gene or any other genetic determinant or factor contributing to a trait.

"Genetic linkage" is understood within the scope of the invention to refer to an association of characters in inheritance due to location of genes in proximity on the same chromosome, measured by percent recombination between loci (centi-Morgan, cM).

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" refers to, in some embodiments, fertilization of one individual by another (e.g., cross-pollination in plants). The term "selfing" refers, in some embodiments, to the production of seed by self-fertilization or self-pollination; i.e., pollen and ovule are from the same plant.

As used herein, the phrase "genetic marker" or "DNA marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

As used herein, the term "genotype" refers to the genetic constitution of a cell or organism. An individual's "genotype for a set of genetic markers" includes the specific alleles, for one or more genetic marker loci, present in the individual's haplotype.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the terms "quantitative trait locus" (QTL) refer to an association between a genetic marker and a chromosomal region and/or gene and/or introgressed sequence that affects the phenotype of a trait of interest. Typically, this is determined statistically; e.g., based on one or more methods published in the literature. A QTL can be a chromosomal region and/or a genetic locus with at least two alleles that differentially affect a phenotypic trait.

The term "recipient watermelon plant" is used herein to indicate a watermelon plant that is to receive DNA obtained from a donor watermelon plant that comprises an introgressed sequence for improved FON 2 resistance.

The term "natural genetic background" is used herein to indicate the original genetic background of genetic sequence. Such a background may for instance be the genome of a wild accession of watermelon. For instance, the genetic sequence of the present invention was found at a specific location on chromosome 10 of a *C. lanatus* subsp. *citroides* plant. Conversely, a method that involves the transfer of DNA, via e.g. breeding, comprising this genetic sequence from chromosome 10 of *C. lanatus* subsp. *citroides* plant to the same position on chromosome 10 of another watermelon species, preferably a cultivated watermelon plant, even more preferably a *C. lanatus* subsp. *lanatus* plant, will result in this genetic sequence not being in its natural genetic background. When the genetic sequence of the present invention is transferred from a *C. lanatus* subsp. *citroides* background into another watermelon species, preferably a cultivated watermelon plant, even more preferably a *C. lanatus* subsp. *lanatus* plant, they are referred to as "introgressed sequence" or "introgressed genetic sequence".

A "donor watermelon plant" is understood within the scope of the invention to mean the watermelon plant which provides the introgressed sequence for improved FON 2 resistance.

"Marker-based selection" is understood within the scope of the invention to refer to e.g. the use of genetic markers to detect one or more nucleic acids from the plant, where the nucleic acid is associated with a desired trait to identify plants that carry alleles for desirable (or undesirable) traits, so that those plants can be used (or avoided) in a selective breeding program.

A single nucleotide polymorphism (SNP), a variation at a single site in DNA, is the most frequent type of variation in the genome. A single-nucleotide polymorphism (SNP) is a DNA sequence variation occurring when a single nucleotide—A, T, C, or G—in the genome (or other shared sequence) differs between members of a biological species or paired chromosomes in an individual. For example, two sequenced DNA fragments from different individuals, AAGCCTA to AAGCTTA, contain a difference in a single nucleotide. In this case there are two alleles: C and T. The basic principles of SNP array are the same as the DNA microarray. These are the convergence of DNA hybridization, fluorescence microscopy, and DNA capture. The three components of the SNP arrays are the array that contains nucleic acid sequences (i.e. amplified sequence or target), one or more labelled allele-specific oligonucleotide probes and a detection system that records and interprets the hybridization signal. The presence or absence of the desired SNP marker allele may be determined by real-time PCR using double-stranded DNA dyes or the fluorescent reporter probe method.

"PCR (Polymerase chain reaction)" is understood within the scope of the invention to refer to a method of producing relatively large amounts of specific regions of DNA or subset(s) of the genome, thereby making possible various analyses that are based on those regions. "PCR primer" is understood within the scope of the invention to refer to relatively short fragments of single-stranded DNA used in the PCR amplification of specific regions of DNA.

"Probe" as used herein refers to a group of atoms or molecules which is capable of recognising and binding to a specific target molecule or cellular structure and thus allowing detection of the target molecule or structure. Particularly, "probe" refers to a labelled DNA or RNA sequence which can be used to detect the presence of and to quantitate a complementary sequence by molecular hybridization.

"Sequence Identity". The terms "identical" or "identity" in the context of two or more nucleic acid or protein sequences, refer to two or more sequences or sub-sequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. As used herein, the percent identity/homology between two sequences is a function of the number of identical positions shared by the sequences (i.e., % identity=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm, as described herein below. For example, sequence identity can be determined conventionally with the use of computer programs such as the Bestfit program (Wisconsin Sequence Analysis Package, Version 8 for Unix, Genetics Computer Group, University Research Park, 575 Science Drive Madison, WI 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequence of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

Embodiments

Plants, Seeds, Fruits.

In a first embodiment, the invention provides a cultivated watermelon plant, preferably a cultivated *Citrullus lanatus* subsp. *lanatus* plant resistant to *Fusarium oxysporum* f. sp. *niveum* race 2 (FON 2) infection, comprising in its genome an introgressed sequence from *C. lanatus* subsp. *citroides* which confers resistance to FON 2, wherein said introgressed sequence is located on chromosome 10 and comprises at least one of the following SNP markers:

a) a G genotype in the heterozygous or homozygous state for SNP marker 1 at a position corresponding to position 129 in SEQ ID NO: 1;

b) an A genotype in the heterozygous or homozygous state for SNP marker 2 at a position corresponding to position 120 in SEQ ID NO: 6;

c) an indel genotype in the heterozygous or homozygous state for SNP marker 3 at a position corresponding to position 164 in SEQ ID NO: 11;

d) an A genotype in the heterozygous or homozygous state for SNP marker 4 at a position corresponding to position 51 in SEQ ID NO: 16;

e) an A genotype in the heterozygous or homozygous state for SNP marker 5 at a position corresponding to position 93 in SEQ ID NO: 21;

f) a C genotype in the heterozygous or homozygous state for SNP marker 6 at a position corresponding to position 135 in SEQ ID NO: 26;

g) an A genotype in the heterozygous or homozygous state for SNP marker 7 at a position corresponding to position 66 in SEQ ID NO: 31;

h) an A genotype in the heterozygous or homozygous state for SNP marker 8 at a position corresponding to position 61 in SEQ ID NO: 36;

i) a G genotype in the heterozygous or homozygous state for SNP marker 9 at a position corresponding to position 83 in SEQ ID NO: 41;

j) an A genotype in the heterozygous or homozygous state for SNP marker 10 at a position corresponding to position 64 in SEQ ID NO: 46;

k) an A genotype in the heterozygous or homozygous state for SNP marker 11 at a position corresponding to position 93 in SEQ ID NO: 51;

l) an A genotype in the heterozygous or homozygous state for SNP marker 12 at a position corresponding to position 83 in SEQ ID NO: 56;

m) a G genotype in the heterozygous or homozygous state for SNP marker 13 at a position corresponding to position 138 in SEQ ID NO: 61;

n) a G genotype in the heterozygous or homozygous state for SNP marker 14 at a position corresponding to position 69 in SEQ ID NO: 66; and/or o) an A genotype in the heterozygous or homozygous state for SNP marker 15 at a position corresponding to position 51 in SEQ ID NO: 71.

Further, the plant of the previous embodiment wherein:

a) the G genotype for SNP marker 1 can be identified in a PCR by amplification of a nucleic acid fragment with a pair of oligonucleotide primers: forward primer of SEQ ID NO: 2 and reverse primer of SEQ ID NO: 5, and probe of SEQ ID NO: 3;

b) the A genotype for SNP marker 2 can be identified in a PCR by amplification of a nucleic acid fragment with a pair of oligonucleotide primers: forward primer of SEQ ID NO: 7 and reverse primer of SEQ ID NO: 10, and probe of SEQ ID NO: 8;

c) the indel genotype for SNP marker 3 can be identified in a PCR by amplification of a nucleic acid fragment with a pair of oligonucleotide primers: forward primer of SEQ ID NO: 12 and reverse primer of SEQ ID NO: 15, and probe of SEQ ID NO: 13;

d) the A genotype for SNP marker 4 can be identified in a PCR by amplification of a nucleic acid fragment with a pair of oligonucleotide primers: forward primer of SEQ ID NO: 17 and reverse primer of SEQ ID NO: 20, and probe of SEQ ID NO: 18;

e) the A genotype for SNP marker 5 can be identified in a PCR by amplification of a nucleic acid fragment with a pair of oligonucleotide primers: forward primer of SEQ ID NO: 22 and reverse primer of SEQ ID NO: 25, and probe of SEQ ID NO: 23;

f) the C genotype for SNP marker 6 can be identified in a PCR by amplification of a nucleic acid fragment with a pair of oligonucleotide primers: forward primer of SEQ ID NO: 27 and reverse primer of SEQ ID NO: 30, and probe of SEQ ID NO: 28;

g) the A genotype for SNP marker 7 can be identified in a PCR by amplification of a nucleic acid fragment with a pair of oligonucleotide primers: forward primer of SEQ ID NO: 32 and reverse primer of SEQ ID NO: 35, and probe of SEQ ID NO: 33;

h) the A genotype for SNP marker 8 can be identified in a PCR by amplification of a nucleic acid fragment with a pair of oligonucleotide primers: forward primer of SEQ ID NO: 37 and reverse primer of SEQ ID NO: 40, and probe of SEQ ID NO: 38;

i) the G genotype for SNP marker 9 can be identified in a PCR by amplification of a nucleic acid fragment with a pair of oligonucleotide primers: forward primer of SEQ ID NO: 42 and reverse primer of SEQ ID NO: 45, and probe of SEQ ID NO: 43;

j) the A genotype for SNP marker 10 can be identified in a PCR by amplification of a nucleic acid fragment with a pair of oligonucleotide primers: forward primer of SEQ ID NO: 47 and reverse primer of SEQ ID NO: 50, and probe of SEQ ID NO: 48;

k) the A genotype for SNP marker 11 can be identified in a PCR by amplification of a nucleic acid fragment with a pair of oligonucleotide primers: forward primer of SEQ ID NO: 52 and reverse primer of SEQ ID NO: 55, and probe of SEQ ID NO: 53;

l) the A genotype for SNP marker 12 can be identified in a PCR by amplification of a nucleic acid fragment with a pair of oligonucleotide primers: forward primer of SEQ ID NO: 57 and reverse primer of SEQ ID NO: 60, and probe of SEQ ID NO: 58;

m) the G genotype for SNP marker 13 can be identified in a PCR by amplification of a nucleic acid fragment with a pair of oligonucleotide primers: forward primer of SEQ ID NO: 62 and reverse primer of SEQ ID NO: 65, and probe of SEQ ID NO: 63;

n) the G genotype for SNP marker 14 can be identified in a PCR by amplification of a nucleic acid fragment with a pair of oligonucleotide primers: forward primer of SEQ ID NO: 67 and reverse primer of SEQ ID NO: 70, and probe of SEQ ID NO: 68; and/or o) the A genotype for SNP marker 15 can be identified in a PCR by amplification of a nucleic acid fragment with a pair of oligonucleotide primers: forward primer of SEQ ID NO: 72 and reverse primer of SEQ ID NO: 75, and probe of SEQ ID NO: 73.

In a further embodiment of the invention, said FON 2 resistance-conferring introgressed sequence comprises at least one of SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, and/or SEQ ID NO: 71, or a sequence that is at least 80%, preferably at least 85%, more preferably at least 90%, even more preferably at least 95% identical to one or more of said sequences while retaining corresponding SNP markers 1 to 15.

In a further embodiment of the invention, said plant comprises at least one of SNP markers 5, 7 and 15. In a further embodiment of the invention, said plant comprises SNP markers and 15.

In a further embodiment of the invention, said plant is heterozygous for said at least one SNP marker. In a further embodiment of the invention, said plant is homozygous for said at least one SNP marker.

In a further embodiment of the invention, said introgressed sequence is comprised in, is obtained from, or is obtainable from *Citrullus lanatus* subsp. *citroides* accession RCAT055816 or from watermelon plant 18WMH505078, representative seed of which is deposited under NCIMB Accession No. 43627, or a progeny or an ancestor thereof.

In a further embodiment, the invention provides a plant according to any of the preceding embodiments wherein said plant is obtained by crossing *Citrullus lanatus* subsp. *citroides* accession RCAT055816 or watermelon plant 18WMH505078, representative seed of which is deposited under NCIMB Accession No. 43627, or a progeny or an ancestor thereof, with a watermelon plant that does not contain said FON 2 resistance-conferring introgressed sequence.

In a further embodiment, the invention provides a plant according to any of the preceding embodiments, wherein said plant is an inbred, a dihaploid, a diploid, a triploid, a tetraploid or a hybrid plant.

In a further embodiment, the invention provides a plant according to any of the preceding embodiments, wherein said plant is triploid and wherein said plant is produced from a cross between a diploid and a tetraploid. In a further embodiment, the invention provides a plant according to any of the preceding embodiments, wherein said plant is produced from a cross between a diploid inbred male parent line and a tetraploid inbred female parent line. In a further embodiment, the invention provides a plant according to any of the preceding embodiments, wherein said plant comprises 3 copies of the introgressed sequence of the invention.

In another embodiment, the plant according to the invention is male sterile. In another embodiment, the plant according to the invention is cytoplasmic male sterile.

In another embodiment, the plant according to the invention grows mature watermelon fruits, wherein the interior flesh of said mature fruits is orange.

In a further embodiment, the watermelon plant of the invention is a watermelon plant according to any of preceding embodiments, wherein said FON 2 resistance-conferring introgressed sequence located on chromosome 10 can be identified using any of the SNP markers 1 to 15 disclosed in Table 4 hereinbelow.

In a further embodiment, the invention provides a cultivated watermelon plant, preferably a cultivated *Citrullus lanatus* subsp. *lanatus* plant resistant to *Fusarium oxysporum* f. sp. *niveum* race 2 (FON 2) infection, comprising in its genome an introgressed sequence from *C. lanatus* subsp. *citroides* which confers resistance to FON 2 located on chromosome 10, wherein said plant genome comprises:

a) a G genotype in the heterozygous or homozygous state for SNP marker 1 at a position corresponding to position 129 in SEQ ID NO: 1, and b) an A genotype in the heterozygous or homozygous state for SNP marker 15 at a position corresponding to position 51 in SEQ ID NO: 71.

In a further embodiment, the cultivated watermelon plant of the previous embodiment further comprises at least a third resistant allele at any of the SNP markers 2 to 14 disclosed in Table 4.

In a further embodiment, the watermelon plant of the invention is a watermelon plant according to any of the preceding embodiments, wherein *Citrullus lanatus* subsp. *citroides* accession RCAT055816 or watermelon plant 18WMH505078, or a progeny or an ancestor thereof, is the source of said FON 2 resistance-conferring introgressed sequence, and wherein a representative seed of plant 18WMH505078 has been deposited under NCIMB Accession No. 43627.

It is a further embodiment to provide a plant part, organ or tissue obtainable from a watermelon plant according to any of preceding embodiments, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the FON 2 resistance trait according to the invention, particularly when grown into a plant that produces fruits.

In a further embodiment, the invention provides a seed that produces a plant according to any of the preceding embodiments.

In a further embodiment the invention relates to the use of a watermelon plant according to any of the preceding embodiments as a watermelon rootstock. In a further embodiment the invention relates to the use of watermelon plant 18WMH505078, representative seed of which is deposited under NCIMB Accession No. 43627, or a progeny or an ancestor thereof as a watermelon rootstock.

In another embodiment is considered the use of a watermelon plant, plant part or seed according to any of the preceding embodiments for producing and harvesting watermelon fruits.

In another embodiment the invention relates to the use of a watermelon plant, plant part or seed according to any embodiments, wherein the watermelon plant, plant part or seed is watermelon plant 18WMH505078, representative seed of which is deposited under NCIMB Accession No. 43627, or a progeny or an ancestor thereof.

In a further embodiment the invention relates to the use of a watermelon plant, plant part or seed according to any of the preceding embodiments to sow a field, a greenhouse, or a plastic house.

In one embodiment, the invention provides watermelon fruits produced by a watermelon plant according to any of the preceding embodiments.

The invention further relates to the use of a watermelon plant according to any of the preceding embodiments to introgress a FON 2 resistance trait into a watermelon plant lacking said FON 2 resistance trait.

The invention further relates to a watermelon plant according to any of the preceding embodiments, wherein said plant further comprises a QTL associated with resistance to FON 1, wherein said QTL is located on chromosome 1, and said QTL is derived from watermelon variety Calhoun Grey.

Genetic Sequences, Markers.

The present invention is further directed to an introgressed genetic sequence linked to the FON 2 resistance trait in the watermelon plant. In a further embodiment, the genetic sequence of the present invention is located on chromosome 10. In a further embodiment of the present invention, the genetic sequence is comprised in, obtained from or obtainable from a donor plant of *Citrullus lanatus* subsp. *citroides* accession RCAT055816 or of watermelon plant 18WMH505078, representative seed of which is deposited under NCIMB Accession No. 43627, or a progeny or an ancestor thereof, and comprising said genetic sequence.

In another embodiment, the introgressed genetic sequence of the present invention is located on chromosome 10 and is characterized by at least one of the following SNP markers:

a) a G genotype in the heterozygous or homozygous state for SNP marker 1 at a position corresponding to position 129 in SEQ ID NO: 1;

b) an A genotype in the heterozygous or homozygous state for SNP marker 2 at a position corresponding to position 120 in SEQ ID NO: 6;

c) an indel genotype in the heterozygous or homozygous state for SNP marker 3 at a position corresponding to position 164 in SEQ ID NO: 11;

d) an A genotype in the heterozygous or homozygous state for SNP marker 4 at a position corresponding to position 51 in SEQ ID NO: 16;

e) an A genotype in the heterozygous or homozygous state for SNP marker 5 at a position corresponding to position 93 in SEQ ID NO: 21;

f) a C genotype in the heterozygous or homozygous state for SNP marker 6 at a position corresponding to position 135 in SEQ ID NO: 26;

g) an A genotype in the heterozygous or homozygous state for SNP marker 7 at a position corresponding to position 66 in SEQ ID NO: 31;

h) an A genotype in the heterozygous or homozygous state for SNP marker 8 at a position corresponding to position 61 in SEQ ID NO: 36;

i) a G genotype in the heterozygous or homozygous state for SNP marker 9 at a position corresponding to position 83 in SEQ ID NO: 41;

j) an A genotype in the heterozygous or homozygous state for SNP marker 10 at a position corresponding to position 64 in SEQ ID NO: 46;

k) an A genotype in the heterozygous or homozygous state for SNP marker 11 at a position corresponding to position 93 in SEQ ID NO: 51;

l) an A genotype in the heterozygous or homozygous state for SNP marker 12 at a position corresponding to position 83 in SEQ ID NO: 56;

m) a G genotype in the heterozygous or homozygous state for SNP marker 13 at a position corresponding to position 138 in SEQ ID NO: 61;

n) a G genotype in the heterozygous or homozygous state for SNP marker 14 at a position corresponding to position 69 in SEQ ID NO: 66; and/or o) an A genotype in the heterozygous or homozygous state for SNP marker 15 at a position corresponding to position 51 in SEQ ID NO: 71.

The present invention discloses a kit for the detection of the FON 2 resistance trait in a watermelon plant, particularly a cultivated watermelon plant, wherein said kit comprises at least one PCR oligonucleotide primer pair and probe, selected from:

a) forward primer of SEQ ID NO: 2 and reverse primer of SEQ ID NO: 5, and probe of SEQ ID NO: 3;

b) forward primer of SEQ ID NO: 7 and reverse primer of SEQ ID NO: 10, and probe of SEQ ID NO: 8;

c) forward primer of SEQ ID NO: 12 and reverse primer of SEQ ID NO: 15, and probe of SEQ ID NO: 13;

d) forward primer of SEQ ID NO: 17 and reverse primer of SEQ ID NO: 20, and probe of SEQ ID NO: 18;

e) forward primer of SEQ ID NO: 22 and reverse primer of SEQ ID NO: 25, and probe of SEQ ID NO: 23;

f) forward primer of SEQ ID NO: 27 and reverse primer of SEQ ID NO: 30, and probe of SEQ ID NO: 28;

g) forward primer of SEQ ID NO: 32 and reverse primer of SEQ ID NO: 35, and probe of SEQ ID NO: 33;

h) forward primer of SEQ ID NO: 37 and reverse primer of SEQ ID NO: 40, and probe of SEQ ID NO: 38;

i) forward primer of SEQ ID NO: 42 and reverse primer of SEQ ID NO: 45, and probe of SEQ ID NO: 43;

j) forward primer of SEQ ID NO: 47 and reverse primer of SEQ ID NO: 50, and probe of SEQ ID NO: 48;

k) forward primer of SEQ ID NO: 52 and reverse primer of SEQ ID NO: 55, and probe of SEQ ID NO: 53;

l) forward primer of SEQ ID NO: 57 and reverse primer of SEQ ID NO: 60, and probe of SEQ ID NO: 58;

m) forward primer of SEQ ID NO: 62 and reverse primer of SEQ ID NO: 65, and probe of SEQ ID NO: 63;

n) forward primer of SEQ ID NO: 67 and reverse primer of SEQ ID NO: 70, and probe of SEQ ID NO: 68; and/or o) forward primer of SEQ ID NO: 72 and reverse primer of SEQ ID NO: 75, and probe of SEQ ID NO: 73.

The present invention also discloses the use of at least one, at least two or at least three of the SNP markers according to the invention for diagnostic selection and/or genotyping of the FON 2 resistance trait locus in a watermelon plant, particularly a cultivated watermelon plant.

The present invention further discloses the use of at least one, at least two or at least three of the SNP markers according to the invention for identifying in a watermelon plant, particularly a cultivated watermelon plant, more particularly a watermelon plant according to the invention, the presence of the FON 2 resistance trait and/or for monitoring the introgression of the FON 2 resistance trait in a watermelon plant, particularly a cultivated watermelon plant, particularly a watermelon plant according to the invention and as described herein. The invention further discloses a polynucleotide (amplification product) obtainable in a PCR reaction involving at least one oligonucleotide primer or a pair of PCR oligonucleotide primers selected from Table 4, which amplification product corresponds to an amplification product obtainable from *Citrullus lanatus* subsp. *citroides* accession RCAT055816 or from watermelon plant 18WMH505078, representative seed of which is deposited under NCIMB Accession No. 43627, or a progeny or an ancestor thereof, comprising the FON 2 resistance-conferring introgressed sequence of the invention.

Also contemplated herein is a polynucleotide that has at least 95%, particularly at least 96%, particularly at least 97%, particularly at least 98%, particularly at least 99% sequence identity with the sequence of said amplification product and/or a polynucleotide exhibiting a nucleotide sequence that hybridizes to the nucleotide sequences of said amplification product obtainable in the above PCR reaction.

The amplification product according to the invention and described herein above can then be used for generating or developing new primers and/or probes that can be used for identifying the FON 2 resistance trait locus.

The present invention therefore further relates in one embodiment to derived markers, particularly to derived primers or probes, developed from an amplification product according to the invention and as described herein above by methods known in the art, which derived markers are genetically linked to the FON 2 resistance trait locus.
Methods of Breeding.

In a further embodiment, the invention provides a method for producing a cultivated watermelon plant, preferably a cultivated *Citrullus lanatus* subsp. *lanatus* plant, exhibiting resistance to FON 2 comprising the steps of a) crossing a plant according to any one of the preceding embodiments with a cultivated watermelon plant lacking said FON 2 resistance-conferring introgressed sequence;

b) selecting a progeny plant comprising said introgressed sequence located on chromosome 10 conferring resistance to FON 2, said selecting step comprising detecting at least one of the following SNP markers:

i) a G genotype in the heterozygous or homozygous state for SNP marker 1 at a position corresponding to position 129 in SEQ ID NO: 1;

ii) an A genotype in the heterozygous or homozygous state for SNP marker 2 at a position corresponding to position 120 in SEQ ID NO: 6;

iii) an indel genotype in the heterozygous or homozygous state for SNP marker 3 at a position corresponding to position 164 in SEQ ID NO: 11;

iv) an A genotype in the heterozygous or homozygous state for SNP marker 4 at a position corresponding to position 51 in SEQ ID NO: 16;

v) an A genotype in the heterozygous or homozygous state for SNP marker at a position corresponding to position 93 in SEQ ID NO: 21;

vi) a C genotype in the heterozygous or homozygous state for SNP marker 6 at a position corresponding to position 135 in SEQ ID NO: 26;

vii) an A genotype in the heterozygous or homozygous state for SNP marker 7 at a position corresponding to position 66 in SEQ ID NO: 31;

viii) an A genotype in the heterozygous or homozygous state for SNP marker 8 at a position corresponding to position 61 in SEQ ID NO: 36;

ix) a G genotype in the heterozygous or homozygous state for SNP marker 9 at a position corresponding to position 83 in SEQ ID NO: 41;

x) an A genotype in the heterozygous or homozygous state for SNP marker at a position corresponding to position 64 in SEQ ID NO: 46;

xi) an A genotype in the heterozygous or homozygous state for SNP marker 11 at a position corresponding to position 93 in SEQ ID NO: 51;

xii) an A genotype in the heterozygous or homozygous state for SNP marker 12 at a position corresponding to position 83 in SEQ ID NO: 56;

xiii) a G genotype in the heterozygous or homozygous state for SNP marker 13 at a position corresponding to position 138 in SEQ ID NO: 61;

xiv) a G genotype in the heterozygous or homozygous state for SNP marker 14 at a position corresponding to position 69 in SEQ ID NO: 66; and/or xv) an A genotype in the heterozygous or homozygous state for SNP marker at a position corresponding to position 51 in SEQ ID NO: 71;

thereby producing a plant with enhanced resistance to FON 2.

In a further embodiment, the invention relates to the method of any of the preceding embodiments, wherein the method further comprises:

c) selfing the selected progeny or crossing the selected progeny with another watermelon plant to produce further progeny.

In a further embodiment, the invention relates to the method of the preceding embodiment, wherein further progeny are selected and selfed/crossed for 2 to 10 more generations.

In a further embodiment, the invention relates to the method of any of the preceding embodiments, wherein the plant of step a) is *Citrullus lanatus* subsp. *citroides* accession RCAT055816 or watermelon plant 18WMH505078, representative seed of which is deposited under NCIMB Accession No. 43627, or a progeny or an ancestor thereof.

In another embodiment the invention relates to a method of providing a FON 2 resistant watermelon plant, plant part or seed, wherein said method comprises the following steps:

a) Crossing a $1^{st}$ plant lacking the FON 2 resistance-conferring introgressed sequence of the invention with a $2^{nd}$ watermelon plant according to any embodiments, b) Obtaining a progeny watermelon plant, and, c) Optionally, selecting a plant of said progeny characterized in that said plant exhibits resistance to FON 2 strain.

In a further embodiment the invention relates to the method of the preceding embodiment wherein the $2^{nd}$ watermelon plant is *Citrullus lanatus* subsp. *citroides* accession RCAT055816 or watermelon plant 18WMH505078, representative seed of which is deposited under NCIMB Accession No. 43627, or a progeny or an ancestor thereof.

In another embodiment the invention relates to a method for producing a FON 2 resistant watermelon plant comprising the following steps:

a) Providing seeds of a watermelon plant according to any of the preceding embodiments, b) Germinating said seed and growing a mature, fertile plant therefrom, c) Inducing self-pollination of said plant under a), growing fruits and harvesting the fertile seeds therefrom, and d) Growing plants from the seeds harvested under c) and selecting a FON 2 resistant watermelon plant.

In another embodiment the invention relates to a method for increasing the resistance to FON 2 of a watermelon plant, comprising the steps of:

a) selecting a watermelon, which comprises a FON 2 resistance trait associated with one introgressed sequence located on chromosome 10, wherein said trait can be identified by the presence of at least one of the SNP markers listed in Table 4;

b) crossing said plant of step a), which comprises a FON 2 resistance trait, with a watermelon plant, particularly a cultivated watermelon plant, which does not comprise a FON 2 resistance trait and shows susceptibility to FON 2, as compared to the plant of step a), and c) selecting progeny from said cross which shows increased FON 2 resistance, as compared to the plant of step b).

In a further embodiment, the invention relates to a method for producing a F1 watermelon plant exhibiting resistance to FON 2, the method comprising crossing an inbred watermelon plant, which is a plant according to any one of the preceding embodiments, with a different inbred watermelon plant to produce F1 hybrid progeny.

Methods of Selection.

In a further embodiment, the invention provides a method for identifying a cultivated watermelon plant, preferably a cultivated *Citrullus lanatus* plant, exhibiting resistance to FON 2 and having at least one copy of said FON 2 resistance-conferring introgressed sequence, said method comprising the step of detecting at least one of the following SNP markers:

a) a G genotype in the heterozygous or homozygous state for SNP marker 1 at a position corresponding to position 129 in SEQ ID NO: 1;

b) an A genotype in the heterozygous or homozygous state for SNP marker 2 at a position corresponding to position 120 in SEQ ID NO: 6;

c) an indel genotype in the heterozygous or homozygous state for SNP marker 3 at a position corresponding to position 164 in SEQ ID NO: 11;

d) an A genotype in the heterozygous or homozygous state for SNP marker 4 at a position corresponding to position 51 in SEQ ID NO: 16;

e) an A genotype in the heterozygous or homozygous state for SNP marker 5 at a position corresponding to position 93 in SEQ ID NO: 21;

f) a C genotype in the heterozygous or homozygous state for SNP marker 6 at a position corresponding to position 135 in SEQ ID NO: 26;

g) an A genotype in the heterozygous or homozygous state for SNP marker 7 at a position corresponding to position 66 in SEQ ID NO: 31;

h) an A genotype in the heterozygous or homozygous state for SNP marker 8 at a position corresponding to position 61 in SEQ ID NO: 36;

i) a G genotype in the heterozygous or homozygous state for SNP marker 9 at a position corresponding to position 83 in SEQ ID NO: 41;

j) an A genotype in the heterozygous or homozygous state for SNP marker 10 at a position corresponding to position 64 in SEQ ID NO: 46;

k) an A genotype in the heterozygous or homozygous state for SNP marker 11 at a position corresponding to position 93 in SEQ ID NO: 51;

l) an A genotype in the heterozygous or homozygous state for SNP marker 12 at a position corresponding to position 83 in SEQ ID NO: 56;

m) a G genotype in the heterozygous or homozygous state for SNP marker 13 at a position corresponding to position 138 in SEQ ID NO: 61;

n) a G genotype in the heterozygous or homozygous state for SNP marker 14 at a position corresponding to position 69 in SEQ ID NO: 66; and/or o) an A genotype in the heterozygous or homozygous state for SNP marker 15 at a position corresponding to position 51 in SEQ ID NO: 71;

thereby identifying a watermelon plant exhibiting resistance to FON 2.

In a further embodiment, the invention relates to the method of the preceding embodiment, wherein said method further comprises selecting a watermelon plant comprising said one or more SNP markers, and crossing the selected watermelon plant with a second watermelon plant to produce progeny watermelon plants that comprise at least one of said SNP markers and exhibits resistance to FON 2.

In another embodiment the invention relates to a method of identifying a watermelon plant comprising the FON 2 resistance-conferring introgressed sequence of the invention, wherein said method comprises the steps of:

a) providing a population segregating for the FON 2 resistance trait, b) screening the segregating population for a member exhibiting resistance to FON 2, wherein said trait can be identified by the presence of FON 2 resistance-conferring introgressed sequence of the invention, c) selecting one member of the segregating population, wherein said member comprises the FON 2 resistance trait.

In a further embodiment, the invention provides a method for identifying a cultivated watermelon plant comprising an introgressed sequence on chromosome 10, wherein said introgressed sequence confers resistance to FON 2, comprising:

a) providing a population segregating for FON 2 resistance, b) screening said population using a kit which detects at least one of the SNP markers listed in Table 4, and, c) identifying a plant comprising said at least one SNP marker selected in the list of Table 4.

In a further embodiment, the invention provides a method for identifying a wild watermelon source of FON 2 resistance trait on chromosome 10, comprising:

a) providing a wild watermelon accession or a plurality of wild watermelon accessions, b) screening said watermelon accession or plurality of wild watermelon accessions using a kit which detects at least one of the SNP markers listed in Table 4, and, c) identifying a wild watermelon accession comprising said at least one SNP marker selected in the list of Table 4.

In yet another embodiment, the invention relates to the use of at least one SNP marker amplified from the genome of a watermelon plant according to any of the preceding embodiments, preferably from the genome of *Citrullus lanatus* subsp. *citroides* accession RCAT055816 or watermelon plant 18WMH505078, representative seed of which is deposited under NCIMB Accession No. 43627, or a progeny or an ancestor thereof, wherein said SNP marker is identified using one of the following kits:

a) forward primer of SEQ ID NO: 2 and reverse primer of SEQ ID NO: 5, and probe of SEQ ID NO: 3;

b) forward primer of SEQ ID NO: 7 and reverse primer of SEQ ID NO: 10, and probe of SEQ ID NO: 8;

c) forward primer of SEQ ID NO: 12 and reverse primer of SEQ ID NO: 15, and probe of SEQ ID NO: 13;

d) forward primer of SEQ ID NO: 17 and reverse primer of SEQ ID NO: 20, and probe of SEQ ID NO: 18;

e) forward primer of SEQ ID NO: 22 and reverse primer of SEQ ID NO: 25, and probe of SEQ ID NO: 23;

f) forward primer of SEQ ID NO: 27 and reverse primer of SEQ ID NO: 30, and probe of SEQ ID NO: 28;

g) forward primer of SEQ ID NO: 32 and reverse primer of SEQ ID NO: 35, and probe of SEQ ID NO: 33;

h) forward primer of SEQ ID NO: 37 and reverse primer of SEQ ID NO: 40, and probe of SEQ ID NO: 38;

i) forward primer of SEQ ID NO: 42 and reverse primer of SEQ ID NO: 45, and probe of SEQ ID NO: 43;

j) forward primer of SEQ ID NO: 47 and reverse primer of SEQ ID NO: 50, and probe of SEQ ID NO: 48;

k) forward primer of SEQ ID NO: 52 and reverse primer of SEQ ID NO: 55, and probe of SEQ ID NO: 53;

l) forward primer of SEQ ID NO: 57 and reverse primer of SEQ ID NO: 60, and probe of SEQ ID NO: 58;

m) forward primer of SEQ ID NO: 62 and reverse primer of SEQ ID NO: 65, and probe of SEQ ID NO: 63;

n) forward primer of SEQ ID NO: 67 and reverse primer of SEQ ID NO: 70, and probe of SEQ ID NO: 68; and/or o) forward primer of SEQ ID NO: 72 and reverse primer of SEQ ID NO: 75, and probe of SEQ ID NO: 73;

and wherein said SNP marker is indicative of the presence of the FON 2 resistance trait in a watermelon plant, to identify a watermelon plant that comprises and exhibits the FON 2 resistance trait.

In a further embodiment, the invention relates to a method for assessing the genotype of a cultivated watermelon plant, preferably a cultivated *Citrullus lanatus* subsp. *lanatus* plant, exhibiting resistance to FON 2, said method comprising the steps of:

a) providing a sample from said plant, and, b) detecting in said sample a QTL locus located on chromosome 10 and associated with said FON 2 resistance, said QTL locus being flanked by SNP markers 1 and 15, and at least one of the following SNP markers:

i) a G genotype in the heterozygous or homozygous state for SNP marker 1 at a position corresponding to position 129 in SEQ ID NO: 1;

ii) an A genotype in the heterozygous or homozygous state for SNP marker 2 at a position corresponding to position 120 in SEQ ID NO: 6;

iii) an indel genotype in the heterozygous or homozygous state for SNP marker 3 at a position corresponding to position 164 in SEQ ID NO: 11;

iv) an A genotype in the heterozygous or homozygous state for SNP marker 4 at a position corresponding to position 51 in SEQ ID NO: 16;

v) an A genotype in the heterozygous or homozygous state for SNP marker at a position corresponding to position 93 in SEQ ID NO: 21;

vi) a C genotype in the heterozygous or homozygous state for SNP marker 6 at a position corresponding to position 135 in SEQ ID NO: 26;

vii) an A genotype in the heterozygous or homozygous state for SNP marker 7 at a position corresponding to position 66 in SEQ ID NO: 31;

viii) an A genotype in the heterozygous or homozygous state for SNP marker 8 at a position corresponding to position 61 in SEQ ID NO: 36;

ix) a G genotype in the heterozygous or homozygous state for SNP marker 9 at a position corresponding to position 83 in SEQ ID NO: 41;

x) an A genotype in the heterozygous or homozygous state for SNP marker at a position corresponding to position 64 in SEQ ID NO: 46;

xi) an A genotype in the heterozygous or homozygous state for SNP marker 11 at a position corresponding to position 93 in SEQ ID NO: 51;

xii) an A genotype in the heterozygous or homozygous state for SNP marker 12 at a position corresponding to position 83 in SEQ ID NO: 56;

xiii) a G genotype in the heterozygous or homozygous state for SNP marker 13 at a position corresponding to position 138 in SEQ ID NO: 61;

xiv) a G genotype in the heterozygous or homozygous state for SNP marker 14 at a position corresponding to position 69 in SEQ ID NO: 66; and/or xv) an A genotype in the heterozygous or homozygous state for SNP marker at a position corresponding to position 51 in SEQ ID NO: 71; and/or xvi) any other DNA marker associated with said QTL locus flanked by SNP markers 1 and 15.

In a further embodiment, the invention relates to a method of identifying in a cultivated watermelon plant, preferably a cultivated *Citrullus lanatus* subsp. *lanatus* plant, an introgressed sequence associated with an increased resistance to FON 2, said method comprising the step of detecting in said plant an allele of at least one DNA marker that is genetically linked to a QTL locus associated with said increased resistance to FON 2, wherein said allele maps within 10 cM, preferably within 5 cM of said QTL locus located on chromosome 10 in a genomic region flanked by SNP markers 1 and 15.

In a further embodiment, the invention relates to the method of the preceding embodiment, wherein said QTL locus can be identified by at least one of the following SNP markers a) a G genotype in the heterozygous or homozygous state for SNP marker 1 at a position corresponding to position 129 in SEQ ID NO: 1;

b) an A genotype in the heterozygous or homozygous state for SNP marker 2 at a position corresponding to position 120 in SEQ ID NO: 6;

c) an indel genotype in the heterozygous or homozygous state for SNP marker 3 at a position corresponding to position 164 in SEQ ID NO: 11;

d) an A genotype in the heterozygous or homozygous state for SNP marker 4 at a position corresponding to position 51 in SEQ ID NO: 16;

e) an A genotype in the heterozygous or homozygous state for SNP marker 5 at a position corresponding to position 93 in SEQ ID NO: 21;

f) a C genotype in the heterozygous or homozygous state for SNP marker 6 at a position corresponding to position 135 in SEQ ID NO: 26;

g) an A genotype in the heterozygous or homozygous state for SNP marker 7 at a position corresponding to position 66 in SEQ ID NO: 31;

h) an A genotype in the heterozygous or homozygous state for SNP marker 8 at a position corresponding to position 61 in SEQ ID NO: 36;

i) a G genotype in the heterozygous or homozygous state for SNP marker 9 at a position corresponding to position 83 in SEQ ID NO: 41;

j) an A genotype in the heterozygous or homozygous state for SNP marker 10 at a position corresponding to position 64 in SEQ ID NO: 46;

k) an A genotype in the heterozygous or homozygous state for SNP marker 11 at a position corresponding to position 93 in SEQ ID NO: 51;

l) an A genotype in the heterozygous or homozygous state for SNP marker 12 at a position corresponding to position 83 in SEQ ID NO: 56;

m) a G genotype in the heterozygous or homozygous state for SNP marker 13 at a position corresponding to position 138 in SEQ ID NO: 61;

n) a G genotype in the heterozygous or homozygous state for SNP marker 14 at a position corresponding to position 69 in SEQ ID NO: 66; and/or o) an A genotype in the heterozygous or homozygous state for SNP marker 15 at a position corresponding to position 51 in SEQ ID NO: 71.

In a further embodiment, the invention relates to the method of the preceding embodiment, wherein said method further comprises the step of selecting a cultivated watermelon plant, preferably a cultivated *Citrullus lanatus* subsp. *lanatus* plant comprising said introgressed sequence.

In a further embodiment, the invention relates to a method of identifying a cultivated watermelon plant, preferably a cultivated *Citrullus lanatus* subsp. *lanatus* plant, exhibiting increased resistance to FON 2 by identifying a QTL associated with said increased resistance to FON 2, the method comprising the steps of:

a) detecting at least one DNA marker from a watermelon plant, which DNA marker is linked to a chromosomal interval associated with increased resistance to FON 2, wherein said chromosomal interval is flanked on each side by SNP markers having at least 80% sequence identity to SEQ ID NOs: 1 and 71; and b) identifying said watermelon plant comprising said at least one DNA marker.

Uses.

The present invention also relates to the use of FON 2 resistance-propagating material obtainable from a watermelon plant according to any of the preceding embodiments for growing a watermelon plant in order to produce FON 2 resistant watermelon plants wherein said FON 2 resistance may be assessed in a standard assay, particularly an assay as described in Example 2 below.

The present invention also relates to the use of FON 2 resistance propagating material obtainable from a watermelon plant according to any of the preceding embodiments for producing watermelon fruits.

The present invention also contemplates the use of the FON 2 resistance genetic sequence of the present invention in association with other genetic sequences associated with FON 2 resistance, for instance those genetic sequences disclosed in WO2009/000736.

In another embodiment the invention relates to the use a cultivated watermelon plant, plant part or seed, more preferably a cultivated *Citrullus lanatus* subsp. *lanatus* plant, plant part or seed according to any of the preceding embodiments for growing a plant and producing and harvesting crops and/or fruits.

In another embodiment the invention relates to the use of a cultivated watermelon plant, more preferably a cultivated *Citrullus lanatus* subsp. *lanatus* plant, according to any of the preceding embodiments for producing fruits for the fresh market or for food processing.

In another embodiment the invention relates to the use of a cultivated watermelon plant, plant part or seed, preferably a cultivated *Citrullus lanatus* subsp. *lanatus* plant, plant part or seed according to any of preceding embodiments, wherein said cultivated watermelon plant, plant part or seed, preferably the cultivated *Citrullus lanatus* subsp. *lanatus* plant, plant part or seed is of watermelon plant 18WMH505078, representative seed of which is deposited under NCIMB Accession No. 43627, or a progeny or an ancestor thereof.

In a further embodiment the invention relates to the use of a cultivated watermelon plant, plant part or seed, more preferably a cultivated *Citrullus lanatus* subsp. *lanatus* plant, plant part or seed according to any of the preceding embodiments to sow a field, a greenhouse, or a plastic house.

In a further embodiment the invention relates to the use of a watermelon plant according to any of the preceding embodiments to confer the increased FON 2 resistance trait to a watermelon plant lacking said trait. The invention further relates to the use of a watermelon plant according to any of the preceding embodiments to introgress an increased FON 2 resistance trait into a watermelon plant lacking said trait.

In a further embodiment the invention relates to the use of any of SEQ ID NOs 1-75 for screening a population of watermelon plants for the presence of a QTL locus located on chromosome 10 and associated with an increased FON 2 resistance.

In a further embodiment the invention relates to the use of any of SEQ ID NOs 1, 6, 11, 16, 21, 26, 31, 36, 41, 46, 51, 56, 61, 66 and 71 for screening a population of watermelon plants for the presence of a QTL locus located on chromosome 10 and associated with an increased FON 2 resistance.

In a further embodiment the invention relates to the use of any of SEQ ID NOs 21, 31 and 71 for screening a population of watermelon plants for the presence of a QTL locus located on chromosome 10 and associated with an increased FON 2 resistance.

Based on the description of the present invention, the skilled person who is in possession of *Citrullus lanatus* subsp. *citroides* accession RCAT055816 or watermelon plant 18WMH505078, representative seed of which is deposited under NCIMB Accession No. 43627, or a progeny or an ancestor thereof, comprising said introgressed genetic sequence, as described herein, has no difficulty to transfer the said introgressed genetic sequence of the present invention to other watermelon plants of various types using breeding techniques well-known in the art with the support of SNP markers herein disclosed.

Seed Deposit Details

Applicant has made a deposit of 2500 seeds of *Citrullus lanatus* plant 18WMH505078 with NCIMB (NCIMB Limited, Ferguson Building, Craibstone Estate, Bucksburn, Aberdeen AB21 9YA, Scotland) on 17 Jun. 2020 under NCIMB Accession No. 43627.

Applicant elects for the expert solution and requests that the deposited material be released only to an Expert according to Rule 32(1) EPC or corresponding laws and rules of other countries or treaties (Expert Witness clause), until the mention of the grant of the patent publishes, or from 20 years from the date of filing if the application is refused, withdrawn or deemed to be withdrawn.

EXAMPLES

Example 1: Germplasm and Population Development

A F1 population resulting from a cross between a *Citrullus lanatus* subsp. *citroides* RCAT055816 accession and an Asian protected type 97103 line was self-pollinated twice via single seed descent to obtain an F3 population. Families from the F3 population were screened for resistance to FON 2 in climatic chambers according to the phenotypic evaluation described in Example 2 below. A QTL associated with increased FON 2 resistance was identified in this F3 population (see Examples 3 to 5).

Molecular markers flanking and spanning the QTL were thereafter used to track the introgression of the QTL into cultivated watermelon lines possessing different genetic backgrounds: 97103, Sugar Baby, Charleston Grey and Allsweet. After sufficient backcrossing to introgress the QTL into these lines and recover desirable agronomic and horticultural traits, self-progeny were generated to produce backcross families homozygous at the QTL locus.

Plant designated as 18WMH505078 derived from the initial F1 population was retained and deposited at NCIMB on 17 Jun. 2020 under NCIMB Accession No. 43627. Plant 18WMH505078 is seed of a watermelon plant heterozygous for the FON 2 resistance trait, i.e., plant 18WMH505078 comprises one copy of the FON 2 resistance-conferring introgressed sequence from the *Citrullus lanatus* subsp. *citroides* plant.

Example 2: Protocols

Example 2A. Fungal Strain

*Fusarium oxysporum* f. sp. *niveum* race 2 (FON 2) isolate culture stocks were maintained on dehydrated sterile filter paper for long term storage. FON 2 was cultured by placing a small square of filter paper with culture on potato dextrose agar (PDA) plates and incubated at 26+2° C. Liquid cultures were grown by transferring a small mycelial plug (about 1 cm diameter) to 1 liter of V8 broth (200 mL V-8 juice, 3.0 g Calcium Carbonate, 15 g Bacto Agar, 800 mL DI-H2O) in a 3 L-Erlenmeyer flask and incubating on a shaker incubator at 70 rpm at 28° C. for 6 days. At 6 days, the mycelial/conidial suspension was filtered through four layers of cheesecloth. Conidia were quantified using a haemocytometer. The conidial concentration was adjusted to 1×106 conidia/mL with sterile distilled H2O.

Example 2B. Preparation and Inoculation of Plants

The F3 population was evaluated for resistance to FON 2 using an artificial inoculation method. Thirty seeds of each line were sown into 50-cell trays containing soil, vermiculite and perlite mixed at 2:1:1 ratio. Thirty seeds from each line were divided into three replicates of ten seeds. Replicates were distributed into separate trays and randomized. In addition, 5 seeds each of Black Diamond, Calhoun Grey and SP-6 cultivars were sown in each tray to use as checks. Seedlings were grown on a greenhouse bench with a photoperiod of 16 h/8 h (day/night). Day time temperature was set at 26+2° C. and night temperature was 24+2° C. Seedlings were inoculated 15 days after planting using FON 2 inoculum prepared as described above. Thirty ml spore suspension was pipetted into each cell of the trays and the trays were placed in a climatic chamber. Plants were grown under fluorescent lights at a diurnal cycle of 16 h/8 h day and night with a temperature of 26+2° C.

Example 2C. Scoring of FON 2 Resistance

The first symptoms such as yellowing of cotyledonary leaves appeared 8-10 days post-inoculation (dpi). Plants were monitored and symptoms were assessed at 14, 18 and 21 dpi. Plants were scored in a quantitative scale as described below.
Rating Symptoms
  9 Healthy plants with no symptoms.
  8 First leaf showing chlorosis symptoms, no vascular discoloration.
  7 Less than 25% leaves showing chlorosis. Stems have no vascular discoloration. Plant growth is normal.
  6 Less than 50% leaves have chlorosis and wilting symptoms. Stems have light vascular discoloration. Plants are not stunted.
  5 Less than 75% leaves have chlorosis and wilting symptoms. Stems have vascular discoloration. Plants are standing.
  4 More than 75% leaves showing chlorosis and wilting, stunted growth. Stems show vascular discoloration.
  3 All leaves wilting, stunted growth.
  2 Leaves and stem collapse.
  1 Plants dead.

All plants were scored on the semi-quantitative rating scale (1-9) above. The disease scores were calculated for each F3 using adjusted mean by line with individual plant scoring using the following calculation:

$$Score = ((R*9)+(S*8)+(T*7)+(U*6)+(V*5)+(W*4)+(X*3)+(Y*2)+(Z*1))/R+S+T+U+V+W+X+Y+Z;$$

wherein

R=number of plants with a score equal to 9;

S=number of plants with a score equal to 8;

T=number of plants with a score equal to 7;

U=number of plants with a score equal to 6;

V=number of plants with a score equal to 5;

W=number of plants with a score equal to 4;

X=number of plants with a score equal to 3;

Y=number of plants with a score equal to 2; and

Z=number of plants with a score equal to 1.

FIG. 1 displays FON 2 pathology assay pictures representative of the disease scale used. Pictures were taken 18 days post inoculation: (1) dead plant, (2) leaf and stem collapse, (3) 100% of leaves are wilting, (4) 75% of leaves are showing symptoms of chlorosis and wilting, vascular discoloration (5) less than 75% of leaves showing symptoms and vascular discoloration, plant still standing upright, (6) less than 50% of leaves showing symptoms and vascular discoloration, (7) less than 25% of leaves showing symptoms and light vascular discoloration, (8) first leaf showing chlorosis symptoms, no vascular discoloration, (9) healthy, no symptoms.

Example 2D. Method of Identifying the QTL and Corresponding Introgressed Sequence Underlying the FON 2 Increased Resistance Trait For QTL discovery, 299 F2 individuals of the "R16× 97103" population were genotyped with 298 genetic markers spanning the genome and a genetic map was calculated. The F3 population derived from self-pollination of each of these 299 F2 individuals were grown and evaluated for FON 2 as described in Example 2A-C above.

The QTL detection was performed using the R/qtl package in the R statistical framework. First, the function 'calc.genoprob' was used to calculate the genotype probabilities (step 1 cM). Haley-Knott regression was performed to provide an approximation of the results of standard interval mapping. Then, the function 'stepwiseqtl' was invoked, which provides a fully automated model selection forward/backward algorithm. LOD threshold for main effect was determine by 10,000 permutations. This algorithm considers different possible interactions (e.g., epistasis). The function 'refineqtl' was used to refine the locations of QTL in the context of a multiple QTL model (maximum likelihood estimates). The function 'fitqtl' was used to fit a defined QTL model and obtain estimates of QTL effects.

Example 3: Identification of One QTL Associated with Increased FON 2 Resistance One QTL was identified based on the FON 2 resistance phenotypes from the F3 population. Table 1 shows the chromosomal location, the effect of the QTL measured as LOD score, and the percentage of variation explained by the QTL on chromosome for FON 2 resistance.

TABLE 1

| Significant QTL associated with FON 2 resistance. | | | |
| --- | --- | --- | --- |
| Chromosome | LOD | % var | Pvalue (F) |
| 10 | 12.2 | 13.1 | 1.83e−12 *** |

"LOD" = log likelihood score, "% var" = percent phenotypic variation explained by the QTL, "Pvalue (F)" = the probability of the QTL detected due to random chance by F test.

The QTL showed a semi-dominant effect in the F3 discovery population. The presence of two copies of the resistant parent alleles at the QTL location is increasing the average disease resistance score from a susceptible score of <3 to a tolerance or resistance score of >6.

Example 4: Introgression of the FON 2 Resistance Conferring Sequence(s) into Commercial Background The *Citrullus lanatus* subsp. *lanatus* plant has soft, red flesh, high fruit flesh Brix at maturity, an Allsweet rind pattern and tiny seeds, whereas *Citrullus lanatus* subsp. *citroides* watermelon plants have white flesh, low brix, extremely firm flesh, and very large seeds, typical of the *citroides* group. The genetic sequence associated with increased resistance to FON 2 strain present in *Citrullus lanatus* subsp. *citroides* watermelon plants was introgressed into Asian protected (97103), Sugar Baby, Crimson Sweet, and Allsweet material by selecting resistant plants after artificial test described in Example 2 and backcrossing them to the respective watermelon types.

The introgressed lines highlighted a similar phenotype to that of the recurrent parent in terms of red flesh and high fruit flesh Brix at maturity while comprising the favourable introgressed sequence for increased FON 2 resistance. The phenotyping results, along with the results of testing for the presence or absence of representative markers in QTL10, are summarized in Table 2 below for the 97013 background.

TABLE 2

| Presence or absence of flanking and characterizing SNP markers for QTL10 and corresponding FON 2 phenotypes. | | | | | |
| --- | --- | --- | --- | --- | --- |
| | | | QTL10 region | | |
| MATID | Line test | 1/SH2496 | 7/SH2488 | 10/SH2513 | 15/SH2486 |
| 1. 16WDL100542 original donor RCAT055816 | 8 | 1 | 1 | 1 | 1 |
| 2. 15WDL200049 recurrent parent 97103 background | 2.7 | 0 | 0 | 0 | 0 |
| 3. 19WDL100848 converted line in 97013 background | 6.4 | 1 | 1 | 1 | 1 |
| 4. 19WDL100846 converted line in 97103 background | 7.1 | 1 | 1 | 1 | 1 |
| 5. 13WDL100650 PI 296341-FR | 7.5 | 0 | 0 | 0 | 0 |
| 6. 15WDL101284 USVL246 | 8 | 0 | 0 | 0 | 0 |

All lines (e.g. line 19WDL100846) comprising the SNP markers spanning and comprising the introgressed sequence underlying QTL10 exhibit increased FON 2 resistance with a disease score >6. This introgressed sequence is specific to the RCAT055816 source, as compared to other sources USVL246 and PI 296341-FR, which can be seen from the use of SNP markers 1, 7, 10 and 15.

Within this region, fifteen SNP markers, SH2496, SH2498, SH2508, SH2506, SH2507, SH2500, SH2488, SH2504, SH2512, SH2513, SH2492, SH2505, SH2493, SH2503 and SH2486 within the QTL interval showed specificity for the selection of donor resistant allele from *Citrullus lanatus* subsp. *citroides* accession RCAT055816 only, and from them, SNP markers SH2488, SH2504, SH2512 and SH2513, were the most closely linked to the resistance.

Table 3 shows both genetic and physical positions of the QTL on chromosome 10 as well as the positions of the fifteen SNP markers tightly linked with the QTL.

TABLE 3

| Genetic map of the QTL on chromosome 10 | | | | |
| --- | --- | --- | --- | --- |
| SNP ID | SNP Locus | Position (CM) | Physical position 97103 v7 (bp) | Observation |
| 1 | SH2496 | 100.2 | 23,418,118 | SNP specific to R allele |
| 2 | SH2498 | | 23,451,657 | SNP specific to R allele |
| 3 | SH2508 | | 23,501,001 | SNP specific to R allele |
| 4 | SH2506 | | 23,509,029 | SNP specific to R allele |
| 5 | SH2507 | | 23,574,864 | SNP specific to R allele |
| 6 | SH2500 | | 23,625,380 | SNP specific to R allele |
| 7 | SH2488 | | 23,650,795 | SNP specific to R allele |
| 8 | SH2504 | | 23,716,145 | SNP specific to R allele |
| 9 | SH2512 | | 23,794,612 | SNP specific to R allele |
| 10 | SH2513 | | 23,836,440 | SNP specific to R allele |
| 11 | SH2492 | | 23,887,046 | SNP specific to R allele |
| 12 | SH2505 | | 23,896,284 | SNP specific to R allele |
| 13 | SH2493 | | 23,937,942 | SNP specific to R allele |
| 14 | SH2503 | | 24,114,787 | SNP specific to R allele |
| 15 | SH2486 | 106.7 | 24,125,048 | SNP specific to R allele |

Example 5: Sequence and SNP Marker Information for QTL10

The sequence information of SNP markers 1 to 15 (SH2496, SH2498, SH2508, SH2506, SH2507, SH2500, SH2488, SH2504, SH2512, SH2513, SH2492, SH2505, SH2493, SH2503 and SH2486), and their respective PCR primers/probes for detection is summarized in Table 4 below.

TABLE 4

| MARKER | 1/SH2496 | 2/SH2498 | 3/SH2508 | 4/SH2506 |
|---|---|---|---|---|
| Resistant (RCAT055816) Allele | G | A | indel | A |
| Susceptible Allele | A | G | G | C |
| Target Sequence: SEQ ID NO. | 1 | 6 | 11 | 16 |
| SNP Position in Target SEQ: nt | 129 | 120 | 164 | 51 |
| Forward Primer: SEQ ID NO. | 2 | 7 | 12 | 17 |
| Reverse Primer: SEQ ID NO. | 5 | 10 | 15 | 20 |
| Probe (Resistant): SEQ ID NO. | 3 | 8 | 13 | 18 |
| Probe (Susceptible): SEQ ID NO. | 4 | 9 | 14 | 19 |

| MARKER | 5/SH2507 | 6/SH2500 | 7/SH2488 | 8/SH2504 |
|---|---|---|---|---|
| Resistant (RCAT055816) Allele | A | C | A | A |
| Susceptible Allele | T | G | C | G |
| Target Sequence: SEQ ID NO. | 21 | 26 | 31 | 36 |
| SNP Position in Target SEQ: nt | 93 | 135 | 66 | 61 |
| Forward Primer: SEQ ID NO. | 22 | 27 | 32 | 37 |
| Reverse Primer: SEQ ID NO. | 25 | 30 | 35 | 40 |
| Probe (Resistant): SEQ ID NO. | 23 | 28 | 33 | 38 |
| Probe (Susceptible): SEQ ID NO. | 24 | 29 | 34 | 39 |

| MARKER | 9/SH2512 | 10/SH2513 | 11/SH2492 | 12/SH2505 |
|---|---|---|---|---|
| Resistant (RCAT055816) Allele | G | A | A | A |
| Susceptible Allele | A | C | G | G |
| Target Sequence: SEQ ID NO. | 41 | 46 | 51 | 56 |
| SNP Position in Target SEQ: nt | 83 | 64 | 93 | 83 |
| Forward Primer: SEQ ID NO. | 42 | 47 | 52 | 57 |
| Reverse Primer: SEQ ID NO. | 45 | 50 | 55 | 60 |
| Probe (Resistant): SEQ ID NO. | 43 | 48 | 53 | 58 |
| Probe (Susceptible): SEQ ID NO. | 44 | 49 | 54 | 59 |

| MARKER | 13/SH2493 | 14/SH2503 | 15/SH2486 |
|---|---|---|---|
| Resistant (RCAT055816) Allele | G | G | A |
| Susceptible Allele | A | A | G |
| Target Sequence: SEQ ID NO. | 61 | 66 | 71 |
| SNP Position in Target SEQ: nt | 138 | 69 | 51 |
| Forward Primer: SEQ ID NO. | 62 | 67 | 72 |
| Reverse Primer: SEQ ID NO. | 65 | 70 | 75 |
| Probe (Resistant): SEQ ID NO. | 63 | 68 | 73 |
| Probe (Susceptible): SEQ ID NO. | 64 | 69 | 74 |

As a matter of example, SNP marker 1 (SH2496) at position 23,418,118 bp on chromosome 10 (based on reference 97103 v7 sequence) is characterized by a particular sequence polymorphism (resistant RCAT055816 vs. susceptible allele) at position 129 of the target sequence of SEQ ID NO: 1. Corresponding forward and reverse primers of SEQ ID NOs 2 and 5, and probes specific for the resistant or susceptible alleles of SEQ ID NOs 3 and 4 are also disclosed.

BIBLIOGRAPHY

Branham S. E. et al., 2017, A GBS-SNP-based linkage map and quantitative trait loci (QTL) associated with resistance to *Fusarium oxysporum* f. sp. *niveum* race 2 identified in *Citrullus lanatus* var. *citroides*, Theor. Appl. Genet. 130:319-330.

Dane F. and Liu J., 2007, Diversity and origin of cultivated and citron type watermelon (*Citrullus lanatus*), Genetic Resources and Crop Evolution, Volume 54, Issue 6, pp 1255-1265.

Fehr W. R., 1987, Principles of cultivar development, theory and technique, Vol. 1, Macmillian Publishing Company.

Food and Agriculture Organization of the United Nations, Statistics Division, FAOSTAT. http://www.fao.org/faostat/en/#home Kihara H., 1951, Triploid watermelons, Proc. Amer. Soc. Hort. Sci., 58:217-230.

Martyn R. D. and Bruton B. D., 1989, An initial survey of the United States for races of *Fusarium oxysporum* f. sp. *niveum*, HortScience 24:696-698.

Martyn R. D. and Netzer D., 1991, Resistance to races 0, 1, and 2 of *Fusarium* wilt of watermelon in *Citrullus* sp. PI-296341-FR, HortScience 26:429-432.

Meru G. and McGregor C. E., 2016, A genetic locus associated with resistance to *Fusarium oxysporum* f. sp. *niveum* race 2 in *Citrullus lanatus*-type watermelon, J. Am. Soc. Hortic. Sci. 141(6):617-622.

Pal S. et al., 2020, Genetic analysis of resistance to *Fusarium oxysporum* f. sp. *niveum* race 2 in cultivated watermelon [*Citrullus lanatus* (Thunb.) Matsum & Nakai], Australasian Plant Pathology 49:319-326.

Ren Y. et al., 2015, Genetic analysis and chromosome mapping of resistance to *Fusarium oxysporum* f. sp. *niveum* (FON) race 1 and race 2 in watermelon (*Citrullus lanatus* L.), Mol. Breeding 35:183.

United States Department of Agriculture, National Agricultural Statistics Service, Vegetables 2019 Summary. https://www.nass.usda.gov/Publications/Todays Reports/reports/vegean20.pdf Wechter W. et al., 2012, Identification of resistance to *Fusarium oxysporum* f. sp. *niveum* race 2 in *Citrullus lanatus* var. *citroides* plant introductions, HortScience 47(3):334-338.

Zhou X. G. et al., 2010, Race 3, a new and highly virulent race of *Fusarium oxysporum* f. sp. *niveum* causing *Fusarium* wilt in watermelon, Plant Dis. 94(1):92-98.

The invention claimed is:

1. A cultivated *Citrullus lanatus* subsp. *lanatus* plant resistant to *Fusarium oxysporum* f. sp. *niveum* race 1,2 (FON 2) infection, comprising in its genome an introgressed sequence from *Citrullus lanatus* subsp. *citroides* which confers resistance to FON 2, wherein said introgressed sequence is comprised in *Citrullus lanatus* subsp. *citroides* accession RCAT055816 or in watermelon plant 18WMH505078, representative seed of which is deposited under NCIMB Accession No. 43627, and wherein said introgressed sequence is located on chromosome 10 and comprises at least the following SNP markers:

a) an A genotype in the heterozygous or homozygous state for SNP marker 7 at a position corresponding to position 66 in SEQ ID NO: 31; and b) an A genotype in the heterozygous or homozygous state for SNP marker 10 at a position corresponding to position 64 in SEQ ID NO: 46.

2. The plant according to claim 1, wherein:

a)

the A genotype for SNP marker 7 can be identified in a PCR by amplification of a nucleic acid fragment with a pair of oligonucleotide primers: forward primer of SEQ ID NO: 32 and reverse primer of SEQ ID NO: 35, and probe of SEQ ID NO: 33; and b) the A genotype for SNP marker 10 can be identified in a PCR by amplification of a nucleic acid fragment with a pair of oligonucleotide primers:

forward primer of SEQ ID NO: 47 and reverse primer of SEQ ID NO: 50, and probe of SEQ ID NO: 48.

3. The plant according to claim 1, wherein said introgressed sequence comprises at least one of SEQ ID NO: 31 or SEQ ID NO: 46, or a sequence that is at least 80% identical to one or both of said sequences.

4. The plant according to claim 1, wherein said plant is homozygous for at least one of SNP marker 7 or SNP marker 10.

5. The plant of claim 1, wherein said plant is obtained by crossing *Citrullus lanatus* subsp. *citroides* accession RCAT055816 or watermelon plant 18WMH505078, representative seed of which is deposited under NCIMB Accession No. 43627, or a progeny or an ancestor thereof, with a watermelon plant that does not contain said FON 2 resistance-conferring introgressed sequence.

6. The plant of claim 1, wherein said plant is an inbred, a dihaploid, a diploid, a triploid, a tetraploid or a hybrid plant.

7. A plant of watermelon plant 18WMH505078, representative seed of which is deposited under NCIMB Accession No. 43627.

8. A plant part of a plant according to claim 1.

9. A seed that produces a plant according to claim 1 or claim 7.

10. A method for producing a cultivated watermelon plant, exhibiting resistance to FON 2 comprising the steps of a) crossing a plant according to claim 1 with a cultivated watermelon plant lacking said FON 2 resistance-conferring introgressed sequence;

b) selecting a progeny plant comprising said introgressed sequence located on chromosome 10 conferring resistance to FON 2, said selecting step comprising detecting at least one of the following SNP markers:

i)

an A genotype in the heterozygous or homozygous state for SNP marker 7 at a position corresponding to position 66 in SEQ ID NO: 31; and ii) an A genotype in the heterozygous or homozygous state for SNP marker 10 at a position corresponding to position 64 in SEQ ID NO: 46;

thereby producing a plant with enhanced resistance to FON 2.

11. The method according to claim 10, wherein the method further comprises:

c) selfing the selected progeny or crossing the selected progeny with another watermelon plant to produce further progeny.

12. The method according to claim 11, wherein further progeny are selected and selfed/crossed for 2 to 10 more generations.

13. A method for producing a F1 watermelon plant exhibiting resistance to FON 2, the method comprising crossing an inbred watermelon plant, which is a plant according to claim 1, with a different inbred watermelon plant to produce F1 hybrid progeny.

14. A method of producing watermelon seed, the method comprising growing a plant from the seed of claim 9, and allowing the plant to produce further seed.

15. The plant according to claim 1, wherein said introgressed sequence comprises at least one of the following SNP markers:

c) a G genotype in the heterozygous or homozygous state for SNP marker 1 at a position corresponding to position 129 in SEQ ID NO: 1;

d) an A genotype in the heterozygous or homozygous state for SNP marker 2 at a position corresponding to position 120 in SEQ ID NO: 6;

e) an indel genotype in the heterozygous or homozygous state for SNP marker 3 at a position corresponding to position 164 in SEQ ID NO: 11;

f) an A genotype in the heterozygous or homozygous state for SNP marker 4 at a position corresponding to position 51 in SEQ ID NO: 16;

g) an A genotype in the heterozygous or homozygous state for SNP marker 5 at a position corresponding to position 93 in SEQ ID NO: 21;

h) a C genotype in the heterozygous or homozygous state for SNP marker 6 at a position corresponding to position 135 in SEQ ID NO: 26;

i) an A genotype in the heterozygous or homozygous state for SNP marker 8 at a position corresponding to position 61 in SEQ ID NO: 36;

j) a G genotype in the heterozygous or homozygous state for SNP marker 9 at a position corresponding to position 83 in SEQ ID NO: 41;

k) an A genotype in the heterozygous or homozygous state for SNP marker 11 at a position corresponding to position 93 in SEQ ID NO: 51;

l) an A genotype in the heterozygous or homozygous state for SNP marker 12 at a position corresponding to position 83 in SEQ ID NO: 56;

m) a G genotype in the heterozygous or homozygous state for SNP marker 13 at a position corresponding to position 138 in SEQ ID NO: 61;

n) a G genotype in the heterozygous or homozygous state for SNP marker 14 at a position corresponding to position 69 in SEQ ID NO: 66; and/or o) an A genotype in the heterozygous or homozygous state for SNP marker 15 at a position corresponding to position 51 in SEQ ID NO: 71.

16. The plant according to claim 1, wherein:

c) the G genotype for SNP marker 1 can be identified in a PCR by amplification of a nucleic acid fragment with a pair of oligonucleotide primers: forward primer of SEQ ID NO: 2 and reverse primer of SEQ ID NO: 5, and probe of SEQ ID NO: 3;

d) the A genotype for SNP marker 2 can be identified in a PCR by amplification of a nucleic acid fragment with a pair of oligonucleotide primers: forward primer of SEQ ID NO: 7 and reverse primer of SEQ ID NO: 10, and probe of SEQ ID NO: 8;

e) the indel genotype for SNP marker 3 can be identified in a PCR by amplification of a nucleic acid fragment with a pair of oligonucleotide primers: forward primer of SEQ ID NO: 12 and reverse primer of SEQ ID NO: 15, and probe of SEQ ID NO: 13;

f) the A genotype for SNP marker 4 can be identified in a PCR by amplification of a nucleic acid fragment with a pair of oligonucleotide primers: forward primer of SEQ ID NO: 17 and reverse primer of SEQ ID NO: 20, and probe of SEQ ID NO: 18;

g) the A genotype for SNP marker 5 can be identified in a PCR by amplification of a nucleic acid fragment with a pair of oligonucleotide primers: forward primer of SEQ ID NO: 22 and reverse primer of SEQ ID NO: 25, and probe of SEQ ID NO: 23;

h) the C genotype for SNP marker 6 can be identified in a PCR by amplification of a nucleic acid fragment with a pair of oligonucleotide primers: forward primer of SEQ ID NO: 27 and reverse primer of SEQ ID NO: 30, and probe of SEQ ID NO: 28;

i) the A genotype for SNP marker 8 can be identified in a PCR by amplification of a nucleic acid fragment with a pair of oligonucleotide primers: forward primer of SEQ ID NO: 37 and reverse primer of SEQ ID NO: 40, and probe of SEQ ID NO: 38;

j) the G genotype for SNP marker 9 can be identified in a PCR by amplification of a nucleic acid fragment with a pair of oligonucleotide primers: forward primer of SEQ ID NO: 42 and reverse primer of SEQ ID NO: 45, and probe of SEQ ID NO: 43;

k) the A genotype for SNP marker 11 can be identified in a PCR by amplification of a nucleic acid fragment with a pair of oligonucleotide primers: forward primer of SEQ ID NO: 52 and reverse primer of SEQ ID NO: 55, and probe of SEQ ID NO: 53;

l) the A genotype for SNP marker 12 can be identified in a PCR by amplification of a nucleic acid fragment with a pair of oligonucleotide primers: forward primer of SEQ ID NO: 57 and reverse primer of SEQ ID NO: 60, and probe of SEQ ID NO: 58;

m) the G genotype for SNP marker 13 can be identified in a PCR by amplification of a nucleic acid fragment with a pair of oligonucleotide primers: forward primer of SEQ ID NO: 62 and reverse primer of SEQ ID NO: 65, and probe of SEQ ID NO: 63;

n) the G genotype for SNP marker 14 can be identified in a PCR by amplification of a nucleic acid fragment with a pair of oligonucleotide primers: forward primer of SEQ ID NO: 67 and reverse primer of SEQ ID NO: 70, and probe of SEQ ID NO: 68; and/or o) the A genotype for SNP marker 15 can be identified in a PCR by amplification of a nucleic acid fragment with a pair of oligonucleotide primers: forward primer of SEQ ID NO: 72 and reverse primer of SEQ ID NO: 75, and probe of SEQ ID NO: 73.

17. The plant according to claim 1, wherein said introgressed sequence comprises at least one of SEQ ID NO: 1, SEQ ID NO: 6, SEQ ID NO: 11, SEQ ID NO: 16, SEQ ID NO: 21, SEQ ID NO: 26, SEQ ID NO: 36, SEQ ID NO: 41, SEQ ID NO: 51, SEQ ID NO: 56, SEQ ID NO: 61, SEQ ID NO: 66, and/or SEQ ID NO: 71, or a sequence that is at least 80% identical to one or more of said sequences.

18. The method according to claim 10, wherein said selecting step of (b) further comprises detecting at least one of the following SNP markers:

iii) a G genotype in the heterozygous or homozygous state for SNP marker 1 at a position corresponding to position 129 in SEQ ID NO: 1;

iv) an A genotype in the heterozygous or homozygous state for SNP marker 2 at a position corresponding to position 120 in SEQ ID NO: 6;

v) an indel genotype in the heterozygous or homozygous state for SNP marker 3 at a position corresponding to position 164 in SEQ ID NO: 11;

vi) an A genotype in the heterozygous or homozygous state for SNP marker 4 at a position corresponding to position 51 in SEQ ID NO: 16;

vii) an A genotype in the heterozygous or homozygous state for SNP marker 5 at a position corresponding to position 93 in SEQ ID NO: 21;

viii) a C genotype in the heterozygous or homozygous state for SNP marker 6 at a position corresponding to position 135 in SEQ ID NO: 26;

ix) an A genotype in the heterozygous or homozygous state for SNP marker 8 at a position corresponding to position 61 in SEQ ID NO: 36;

x) a G genotype in the heterozygous or homozygous state for SNP marker 9 at a position corresponding to position 83 in SEQ ID NO: 41;

xi) an A genotype in the heterozygous or homozygous state for SNP marker 11 at a position corresponding to position 93 in SEQ ID NO: 51;

xii) an A genotype in the heterozygous or homozygous state for SNP marker 12 at a position corresponding to position 83 in SEQ ID NO: 56;

xiii) a G genotype in the heterozygous or homozygous state for SNP marker 13 at a position corresponding to position 138 in SEQ ID NO: 61;

xiv) a G genotype in the heterozygous or homozygous state for SNP marker 14 at a position corresponding to position 69 in SEQ ID NO: 66; and/or xv) an A genotype in the heterozygous or homozygous state for SNP marker 15 at a position corresponding to position 51 in SEQ ID NO: 71.

19. The method according to claim 10, wherein the cultivated watermelon plant is a cultivated *Citrullus lanatus* subsp. *lanatus* plant.

\* \* \* \* \*